United States Patent [19]
Mizuno et al.

[11] Patent Number: 5,397,780
[45] Date of Patent: Mar. 14, 1995

[54] PYRROLOAZEPINE DERIVATIVE

[75] Inventors: Akira Mizuno, Kyoto; Hidetsura Cho, Ibaraki; Mikiko Miya, Tsukuba; Toshio Tatsuoka, Nishinomiya; Takafumi Ishihara, Takatsuki, all of Japan

[73] Assignee: Suntory Limited, Osaka, Japan

[21] Appl. No.: 30,268

[22] PCT Filed: Aug. 6, 1992

[86] PCT No.: PCT/JP92/01008
§ 371 Date: Apr. 6, 1993
§ 102(e) Date: Apr. 6, 1993

[87] PCT Pub. No.: WO87/07274
PCT Pub. Date: Dec. 3, 1987

[51] Int. Cl.$^6$ .................. A61K 31/55; C07D 487/04
[52] U.S. Cl. .................. 514/215; 540/215
[58] Field of Search .............. 540/521; 340/521; 514/215

[56] References Cited

U.S. PATENT DOCUMENTS

| | | |
|---|---|---|
| 3,563,979 | 2/1971 | Hester, Jr. . |
| 3,573,323 | 3/1971 | Hester, Jr. . |
| 3,573,324 | 3/1971 | Hester, Jr. . |
| 5,206,239 | 4/1993 | Mizuno et al. . |

FOREIGN PATENT DOCUMENTS

| | | |
|---|---|---|
| 39 03 368 | 8/1990 | Germany . |
| 62-161786 | 7/1987 | Japan . |
| 2-500738 | 3/1990 | Japan . |
| WO87/07274 | 12/1987 | WIPO . |

OTHER PUBLICATIONS

Journal of Natural Products, vol. 48, No. 1, pp. 47–53 (1985), Schmitz et al.
Aust. J. Chem., vol. 43, 1990, pp. 355–365, B. Kasum, et al., "Dihydroindol-7(6H)-Ones and 6,7-Dihydropyrrolo[2,3-c]azepine-4,8(1H,5H)-dione".
Chemical Abstracts, vol. 102, 1985, AN-146334h, N. K. Utkina, et al., "Nitrogen-Containing Metabolites of the Marine Sponge *Acanthella carteri*".
Tetrahedron, vol. 41, No. 24, pp. 6019–6033, 1985, G. De Nanteuil, et al., "Invertebres Marins Du Lagon Neo-Caledonien-V1", (with English Abstract).
Journal of The Chemical Society, pp. 435 & 436, Jan. 3, 1980, G. Sharma, et al., "Characterizaton of a Yellow Compound Isolated from the Marine Sponge *Phakellia flabellata*".

*Primary Examiner*—Robert T. Bond
*Attorney, Agent, or Firm*—Oblon, Spivak, McClelland, Maier & Neustadt

[57] ABSTRACT

This invention provides a pyrroloazepine derivative represented by the following formula (I):

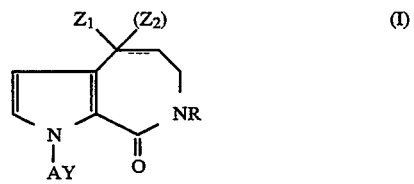

where the substituents are defined in the specification. The pyrroloazepine derivatives according to the present invention are drugs having excellent anti-$\alpha_1$ action and anti-serotonin action and feature high safety. They can therefore be used, for example, as novel therapeutics for circulatory diseases.

12 Claims, No Drawings

PYRROLOAZEPINE DERIVATIVE

TECHNICAL FIELD

The present invention relates to novel pyrroloazepine derivatives, and more specifically to novel pyrroloazepine derivatives and salts thereof, said derivatives and salts having strong anti-$\alpha_1$ action and anti-serotonin action moreover low toxicity and being useful as therapeutics for circulatory diseases such as hypertension and congestive heart failure, their preparation processes and therapeutics for circulatory diseases, said therapeutics containing them as active ingredients.

BACKGROUND ART

Numerous substances have heretofore been known as drugs which act on the circulatory system. Among these, a variety of substances have been developed as antihypertensive drugs.

Of such drugs as employed as circulatory drugs, $\alpha_1$-blockers are accompanied by the drawback that they generally have side effects such as orthostatic disorder and reflex tachycardia, tend to induce orthostatic hypotension especially when administered to aged people and hence require attention.

As drugs having less tendency of inducing such side effects of $\alpha_1$-blockers, on the other hand, certain drugs having both anti-serotonin action and anti-$\alpha_1$ action have been developed as drugs effective for senile hypertension and the like. However, these drugs may not be able to exhibit, for example, sufficient hypotensive action in some instances, and their side effects to the central nervous system such as drowsiness and sedative action have posed problems.

DISCLOSURE OF THE INVENTION

In view of the foregoing circumstances, the present inventors synthesized numerous compounds and investigated their pharmacological effects with a view toward obtaining drugs having both anti-serotonin action and anti-$\alpha_1$ action, strong hypotensive action, and low side effects and toxicity.

As a result, the compounds represented by the below-described formula (I) having the pyrroloazepine structure have been found to meet the above requirements, leading to the completion of the present invention.

This invention therefore provides a pyrroloazepine derivative represented by the following formula (I):

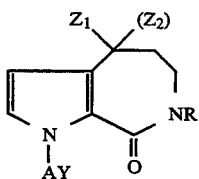
(I)

wherein the dashed line indicates the presence or absence of a bond and when the bond indicated by the dashed line is present, $Z_1$ represents a hydrogen atom but, when the bond indicated by the dashed line is absent, $Z_1$ represents a hydrogen atom and $Z_2$ represents a hydroxyl group or $Z_1$ and $Z_2$ are taken together to form an oxygen atom or a group $NOR_1$, in which $R_1$ represents a hydrogen atom, an alkyl group, a substituted or unsubstituted aryl group or a substituted or unsubstituted aralkyl group; R represents a hydrogen atom, an alkyl group, a substituted or unsubstituted cycloalkyl group, a substituted or unsubstituted cycloalkyl-alkyl group, a substituted or unsubstituted aryl group, or a substituted or unsubstituted aralkyl group; A represents an alkylene, alkenylene or alkynylene group with one of hydrogen atoms being substituted or unsubstituted by a hydroxyl group; and Y represents a group:

in which $R_2$ and $R_3$ may be the same or different and individually represent a hydrogen atom, an alkyl group which may be substituted by a lower alkoxy group or a substituted or unsubstituted, aryloxyl group, a substituted or unsubstituted aryl group, a substituted or unsubstituted aralkyl group or a partially-saturated naphthyl group, or a group:

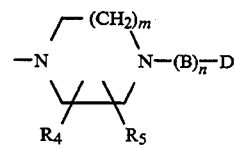

in which $R_4$ and $R_5$ may be the same or different and individually represent a hydrogen atom or an alkyl group, B represents a carbonyl group, a sulfonyl group, an alkylene group, an alkenylene group or a substituted or unsubstituted phenylmethylene group, m stands for 1 or 2, n stands for 0 or 1, and D represents an alkoxy group, a substituted or unsubstituted aromatic heterocyclic group, a substituted or unsubstituted aryl group or a 1,4-benzodioxanyl group, or a salt thereof; a preparation process thereof; and a therapeutic for circulatory diseases, said therapeutic containing as an active ingredient the pyrroloazepine derivative or the salt thereof.

BEST MODES FOR CARRYING OUT THE INVENTION

In the pyrroloazepine derivative (I) of the present invention, preferred examples of group R include a hydrogen atom, branched or linear $C_{1-8}$ alkyl groups such as methyl, ethyl, propyl, isopropyl and pentyl groups; substituted or unsubstituted $C_{3-8}$ cyclolalkyl groups such as cyclopropyl, cyclopentyl and cyclohexyl groups; substituted or unsubstituted $C_{3-8}$ cycloalkylalkyl groups such as cyclopropylmethyl, cyclohexylmethyl and cyclohexylethyl groups; aryl groups such as a phenyl group, phenyl groups substituted by one or more halogen atoms such as fluorine, chlorine and bromine, $C_{1-4}$ alkyl groups such as methyl and ethyl groups and/or $C_{1-4}$ alkoxy groups such as methoxy and ethoxy groups, and a naphthyl group; and aralkyl groups such as diphenylmethyl, benzyl and phenethyl groups. In this case, each aromatic ring may be substituted by one or more of the halogen atoms, alkyl groups and/or alkoxy groups referred to above. Among them, methyl and benzyl groups are particularly preferred.

In addition, preferred examples of group A include branched or linear $C_{2-10}$ alkylene groups, in which one of the hydrogen atoms may be substituted by a hydroxyl group, such as ethylene, trimethylene, tetramethylene, pentamethylene, octamethylene, 3,3-dimethylpentamethylene and 2-hydroxypropylene groups; branched or linear $C_{4-10}$ alkenylene groups such as 2-butenylene and 3-pentenylene groups; and branched or linear $C_{4-10}$ alkynylene groups such as 2-butynylene, 2-pentynylene and 3-pentynylene groups. Among them, ethylene, trimethylene, tetramethylene, pentamethylene, octamethylene and 2-hydroxypropylene groups are particularly preferred.

Further, preferred examples concerning groups $Z_1$ and $Z_2$ include that inducing no bond indicated by the dashed line and containing a hydrogen atom as $Z_1$ and a hydroxyl group as $Z_2$ and those where $Z_1$ and $Z_2$ are taken together to form an oxygen atom or a group $-NOR_1$. Among them, particularly preferred are those where $Z_1$ and $Z_2$ are taken together to form an oxygen atom or a group $-NOR_1$. Preferred examples of $R_1$ in the group $-NOR_1$ include a hydrogen atom; branched or linear $C_{1-4}$ alkyl groups such as methyl, ethyl and isopropyl groups; aryl groups such as a phenyl group, phenyl groups substituted by one or more of the halogen atoms, alkyl groups and/or alkoxy groups referred to above, and a naphthyl group; and aralkyl groups such as benzyl and diphenylmethyl groups. In this case, each aromatic ring may be substituted by one or more of the halogen atoms, alkyl groups and/or alkoxy groups referred to above. Among these, a hydrogen atom is particularly preferred.

Furthermore, preferred examples of group —Y include heterocyclic groups led by a piperazine group and a homopiperazine group. These heterocyclic groups may each be substituted. The following heterocyclic groups can be given as more preferred examples.

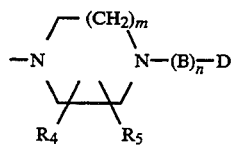

wherein $R_4$ and $R_5$ individually represent a hydrogen atom or a branched or linear alkyl group (preferably a hydrogen atom or a lower alkyl group such as a methyl or ethyl group); B represents a carbonyl group, a sulfonyl group, a branched or linear alkylene group (preferably a methylene group), an alkenylene group (preferably a 2-propenylene group) or a Substituted or unsubstituted phenylmethylene group; D represents an alkoxy group (preferably a lower alkoxy group such as a methoxyl or ethoxyl group), a substituted or unsubstituted aromatic heterocyclic group (preferably a pyridyl, pyrimidyl or furanyl group); a substituted or unsubstituted aryl group (preferably a phenyl group or a phenyl group substituted by one or more hydroxyl groups, benzyloxy groups, the above-described halogen atoms, the above-described alkyl groups and/or the above-described alkoxy groups) or 1,4-benzodioxanyl group; m stands for 1 or 2; and n stands for 0 or 1.

When Y represents a group:

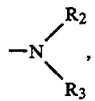

on the other hand, preferred examples of $R_2$ and $R_3$ are a hydrogen atom and a phenoxyethyl group, respectively.

Many of the compounds (I) according to the present invention have isomers. It is to be noted that these isomers are all embraced by the present invention. For example, when there is a hydroxyimino group or an O-substituted hydroxyimino group at 4-position of the pyrroloazepine ring, there are both an (E)-isomer and a (Z) isomer with respect to the group. The compounds of the present invention also include these individual isomers and their mixtures.

Various processes can be employed for the preparation of the pyrroloazepine derivatives (I) according to the present invention. It is however preferable to prepare the pyrroloazepine derivatives (I), for example, by any of the following processes.

PROCESS 1

Among the pyrroloazepine derivatives (I), each compound (Ia) in which $Z_1$ and $Z_2$ are taken together to form an oxygen atom can be obtained in accordance with the following reaction scheme, namely, by converting the compound represented by formula (II) to the compound represented by formula (IV) and then reacting the compound (IV) with the nitrogen-containing compound represented by formula (V) or a salt thereof.

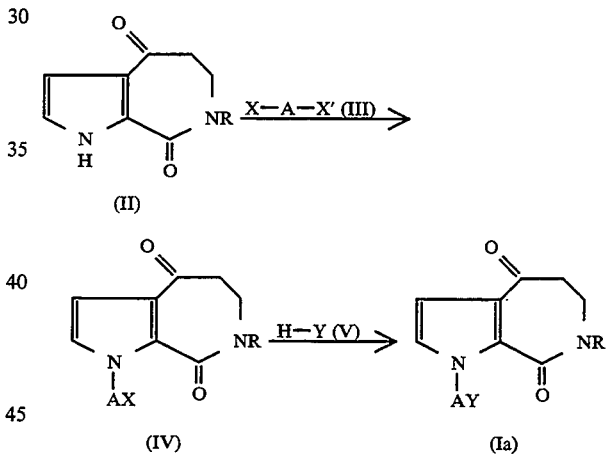

wherein A, R and Y have the same meanings as defined above, X and X' may be the same or different and individually represent a substituent easily replaceable with an amino group.

The conversion from the compound (II) to the compound (IV) is effected by causing the compound represented by formula (III) to act on the compound (II) in the presence of an organic or inorganic base.

Examples of the substituent, which is easily replaceable with an amino group, as group X or X' in the compound (III) include halogen atoms such as chlorine and bromine atoms, alkylsulfonyloxy groups such as a methanesulfonyloxy group, and arylsulfonyloxy groups such as p-toluenesulfonyloxy group. Any solvent can be used in this reaction as long as it does not take part in the reaction. Illustrative solvents include dimethylformamide, acetonitrile, dimethylsulfoxide, tetrahydrofuran, dioxane, acetone and 2-butanone. Further, exemplary organic or inorganic bases include triethylamine, pyridine, collidine, 1,8-diazabicyclo[5.4.0]undec-7-ene (DBU), sodium hydroxide, potassium hydroxide, sodium carbonate, potassium carbonate, sodium ethoxide, and potassium t-butoxide. The reaction is conducted at −20° C. to reflux temperature.

To prepare the compound (Ia) by reacting the compound (IV) with the nitrogen-containing compound (V), it is only necessary to react the nitrogen-containing compound (V) or an organic acid or inorganic acid salt thereof with the compound (III), optionally together with an organic base such as triethylamine, pyridine, collidine, DBU or potassium t-butoxide or an inorganic base such as potassium carbonate, sodium carbonate, potassium hydroxide or sodium hydroxide, optionally after adding an iodide such as sodium iodide or potassium iodide, at room temperature to 150° C. in a solventless manner or in a solvent such as dimethylformamide, acetonitrile, dimethylsulfoxide, methanol, ethanol or 1-butanol.

Examples of the nitrogen-containing compound (V) include dimethylamine, isopropylamine, t-butylamine, 3-phenylpropylamine, 2-phenoxyethylamine, N-propyl-2-(8-hydroxy-1,2,3,4-tetrahydronaphthyl)amine, 1-phenylpiperazine, 1-(2-methoxyphenyl)piperazine, 1-(3-methoxyphenyl)piperazine, 1-(4-methoxyphenyl)piperazine, 1-(2-chlorophenyl)piperazine, 1-(3-chlorophenyl)piperazine, 1-(4-chlorophenyl)piperazine, 1-(4-fluorophenyl)piperazine, 1-(2-pyridyl)piperazine, 1-(2-pyrimidyl)piperazine, 1-benzylpiperazine, 1-diphenylmethylpiperazine, 1-cinnamylpiperazine, 1-(1,4-benzodioxan-2-ylmethyl)piperazine, 1-benzoylpiperazine, 1-(4-benzyloxybenzoyl)piperazine, 1-(4-hydroxybenzoyl)piperazine, 2-furoylpiperazine and 1-ethoxycarbonylpiperazine. They are all either known compounds or compounds which can be readily prepared by a known process or a process similar to the known process.

Incidentally, among the compounds (II) employed as starting materials in the above reaction, the compound in which R is H has been known but the remaining compounds are novel compounds. These novel compounds can each be prepared in accordance with the following reaction scheme, namely, by reacting a pyrrole-2-carboxylic acid or a derivative thereof represented by the formula (XI) with a β-amino acid or a derivative thereof, represented by the formula (XII), or an organic or inorganic salt of the β-amino acid or the derivative thereof and optionally removing the protecting group, thereby obtaining the compound represented by the formula (XIII) and then ring-closing this compound.

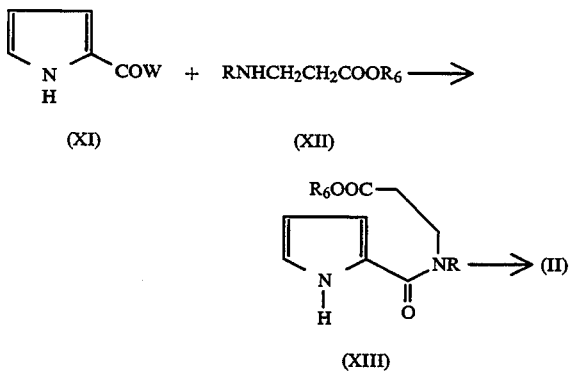

wherein R has the same meaning as defined above, $R_6$ represents a hydrogen atom or a carboxyl-protecting group, and W represents a hydroxyl group or a substituent easily replaceable with an amino group.

Examples of the substituent easily replaceable with an amino group as represented by W in the compound (XI) include halogen atoms, carboxylic acid residue and the like. On the other hand, as the carboxyl-protecting group of the group $R_6$ in the compound (XII), it is possible to use, in addition to lower alkyl groups such as methyl, ethyl, n-propyl, isopropyl, n-butyl, isobutyl and t-butyl and $C_{7-20}$ aralkyl groups such as benzyl and 9-anthrylmethyl, the conventional protecting groups described by T. W. Greene in "Protective Groups in Organic Synthesis" (John Wiley & Sons, Inc.) and the like.

For the synthesis of the compounds (XIII), it is possible to use any one of the various processes disclosed in "Compendium of Organic Synthetic Methods" (WILEY-INTERSCIENCE; A Division of John Wiley & Sons, Inc.) and the like. Illustrative processes include the process in which pyrrole-2-carboxylic acid of the compound (XI) in which W is OH is treated with an organic compound such as diethyl cyanophosphonate (DECP), diphenylphosphoryl azide (DPPA), dicyclohexylcarbodiimide (DCC), 1-ethyl-3-(3-dimethylaminopropyl)carbodiimide hydrochloride or 2-iodo-1-methylpyridinium iodide or an inorganic compound such as silicon tetrachloride or tin tetrachloride, if necessary, in the presence of an organic or inorganic base; and the process in which pyrrole-2-carboxylic acid is reacted after converting it to its acid halide, symmetric acid anhydride, mixed acid anhydride, its active ester such as p-nitrophenyl ester, or the like.

Each compound (XIII) thus obtained is subjected to a cyclization reaction, optionally after removing the protecting group by virtue of a suitable method such as the action of an acid or a base, or catalytic reduction.

This cyclization reaction is conducted by treating the compound (XIII) together with an organic acid such as methanesulfonic acid, an inorganic acid such as sulfuric acid or polyphosphoric acid or a mixture of such an organic or inorganic acid and phosphorus pentoxide at room temperature to 170° C., preferably at 80°–120° C.

In this case, a solvent which does not take part in the reaction may be added as needed.

As an alternative, the cyclizing reaction can also be practiced by, optionally after adding a catalyst, treating the compound (XIII) with oxalyl chloride, thionyl chloride, thionyl bromide, oxalyl bromide, phosgene, phosphorus trichloride, phosphorus tribromide, phosphoryl chloride, phosphoryl bromide or the like to convert the compound (XIII) to its corresponding acid halide and then treating the acid halide at −20° C. to reflux temperature in the presence of a Lewis acid such as aluminum chloride, aluminum bromide, boron trifluoride-ether complex or tin tetrachloride in a solvent such as dichloromethane, 1,2-dichloroethane or nitromethane or heating the acid halide in acetic acid.

The compounds (II) obtained in the above manner can be used directly as starting materials for the preparation of the compounds (I) of the present invention. They can also be used after purification by a conventional purification method, for example, by recrystallization or column chromatography if necessary.

PROCESS 2

Among the pyrroloazepine derivatives (I), each compound (Ib) in which $Z_1$ and $Z_2$ are coupled together to form a group $NOR_1$ can be prepared in accordance with the following reaction formula, namely, (i) by causing a hydroxylamine or a derivative thereof represented by the formula (VI) or a salt of the hydroxylamine or the derivative to act on the compound (Ia) obtained by the above-described reaction or (ii) by causing the hydroxylamine or its derivative (VI) or a salt of the hydroxylamine or the derivative to act on the compound (IV) and then causing a nitrogen-containing compound (V) or a salt thereof to act further.

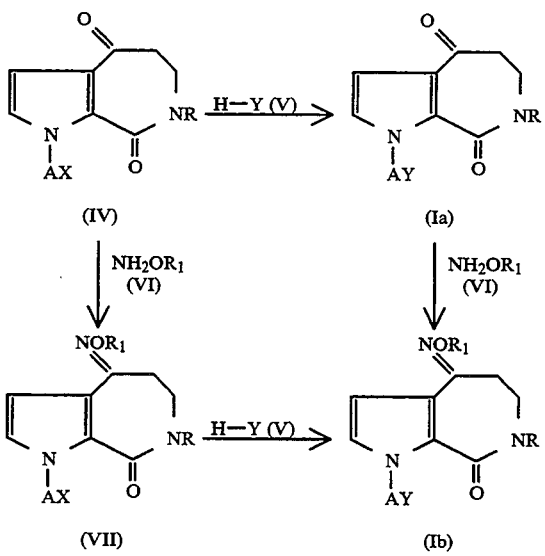

wherein A, R, $R_1$, X and Y have the same meanings as defined above.

The reaction between the compound (Ia) or (IV) and the hydroxylamine or its derivative (VI) is practiced, if necessary, in the presence of an organic base such as pyridine, triethylamine, collidine, DBU, sodium acetate or potassium acetate or an inorganic base such as potassium carbonate or sodium hydroxide. The hydroxylamine or its derivative (VI) may also be used in the form of an organic acid salt or an inorganic acid salt.

The reaction is conducted at 0° C. to reflux temperature, preferably 0° C.–100° C. optionally in a suitable solvent such as methanol, ethanol, propanol, tetrahydrofuran, dimethylformamide or dimethylsulfoxide.

The compound (VII) obtained by the reaction of the compound (IV) with the compound (VI) can be reacted further with the nitrogen-containing compound (V) by the method described above, whereby the compound (VII) can be converted to the compound (Ib).

Upon preparation of the compound (Ib), it is determined depending on the structure and properties of the nitrogen-containing compound (V) whether the hydroxylamine or its derivative (VI) should be reacted to the compound (IV) or to the compound (Ia).

Where there is a group reactive to the hydroxylamine or its derivative (VI), such as a carbonyl group, in the nitrogen-containing compound (V), it is desirable to choose the process that the hydroxylamine or its derivative (VI) is reacted to the compound (IV).

PROCESS 3

Among the pyrroloazepine derivatives (I), each compound (Ic) in which $Z_1$ and $Z_2$ are taken together to form an oxygen atom and group A represents —A'—CH(OH)CH$_2$—, in which A' represents an alkylene group, can be prepared in accordance with the following reaction formula, namely, by converting the compound represented by the formula (II) to a compound represented by the formula (IX) and then, causing a nitrogen-containing compound (V) or a salt thereof to act on the compound (IX).

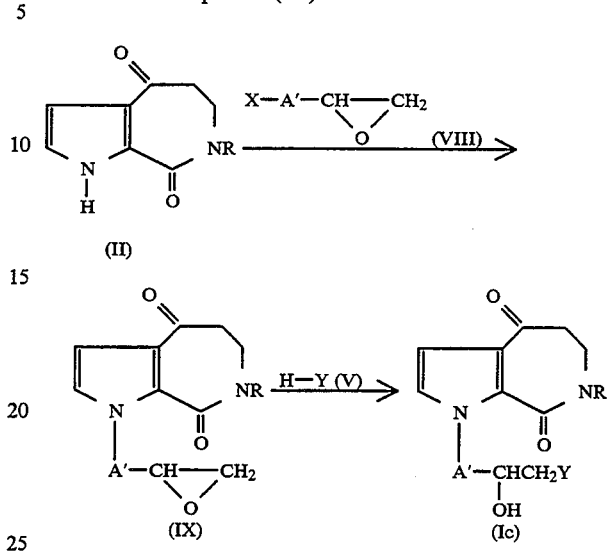

wherein A', R, X and Y have the same meanings as defined above.

The conversion from the compound (II) to the compound (IX) is effected by causing the compound represented by formula (VIII) to act on the compound (II) in the presence of an organic or inorganic base. The conversion can be conducted in exactly the same manner as that employed for the above-described conversion from the compound (II) to the compound (IV).

To prepare the compound (Ic) by reacting the compound (IX) with the nitrogen-containing compound (V), it is only necessary to react, at room temperature to reflux temperature, in a solventless manner or in a solvent such as dimethylformamide, acetonitrile, dimethylsulfoxide, toluene, methanol, ethanol or 1-butanol, the nitrogen-containing compound (V) or an organic acid or inorganic acid salt thereof with the compound (IX), optionally together with an organic base such as triethylamine, pyridine, collidine, DBU or potassium t-butoxide or an inorganic base such as potassium carbonate, sodium carbonate, potassium hydroxide or sodium hydroxide.

PROCESS 4

Among the pyrroloazepine derivatives (I), each compound (Ia) in which $Z_1$ and $Z_2$ are taken together to form an oxygen atom can be prepared by reacting the compound, which is represented by the formula (II), with the nitrogen-containing compound represented by the formula (X) or its salt in accordance with the following reaction formula.

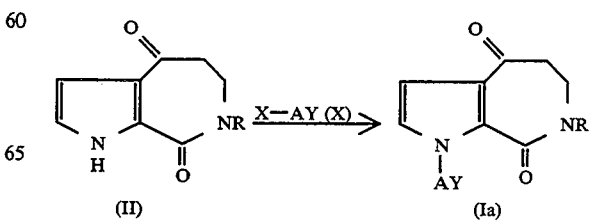

wherein A, R, X and Y have the same meanings as defined above.

The conversion from the compound (II) to the compound (Ia) can be conducted in exactly the same manner as that employed for the conversion from the compound (IV) to the compound (Ia) in Process 1.

PROCESS 5

Among the pyrroloazepine derivatives (I), each compound (Id) in which $Z_1$ represents a hydrogen atom and $Z_2$ represents a hydroxyl group can be prepared by reducing the compound (Ia), which has been obtained following the above reaction formula, in accordance with the following reaction formula.

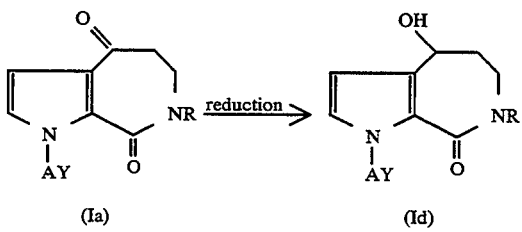

(Ia)                (Id)

wherein A, R and Y have the same meanings as defined above.

The above reaction is effected by reducing the compound represented by formula (Ia) with a reducing agent such as sodium borohydride, potassium borohydride, sodium cyanoborohydride or tri-n-butyltin hydride, in an ordinarily used solvent, at $-78°$ C. to reflux temperature, preferably at $-20°$ C. to room temperature.

The conversion from the compound (Ia) to the compound (Id) can also be effected by catalytic reduction which uses Raney nickel or the like.

PROCESS 6

Among the pyrroloazepine derivatives (I), each compound (Ie) in which the bond indicated by a dashed line exists, namely, a double bond exists and $Z_1$ represents a hydrogen atom can be prepared by subjecting the compound (Id), which has been obtained by the above reaction, to dehydration in accordance with the following reaction formula.

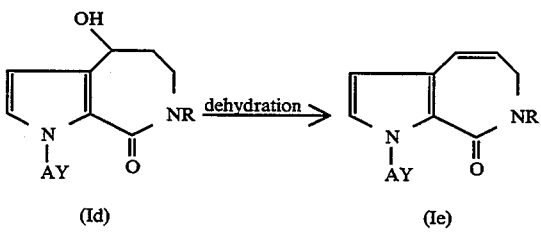

(Id)                (Ie)

wherein A, R and Y have the same meanings as defined above.

The above reaction is conducted by treating the compound (Id) together with an acid such as hydrogen chloride, hydrogen bromide, sulfuric acid, methanesulfonic acid, p-toluenesulfonic acid or the like, optionally in a solvent such as water, methanol, ethanol, chloroform, toluene or ethyl acetate, at $-20°$ C. to 100° C., preferably at $-20°$ C. to room temperature.

As an alternative, the conversion from the compound represented by the formula (Id) to the compound (Ie) is effected by causing methanesulfonyl chloride, p-toluenesulfonyl chloride, phosphorus trichloride, phosphorus oxychloride, thionyl chloride or the like and a base such as triethylamine, collidine or pyridine to act on the compound (Id), if necessary in a solvent such as dichloromethane, chloroform or toluene.

If necessary, the compounds (I) of the present invention obtained as described above can be reacted with various acids to convert the compounds (I) to their salts, followed by purification by a method such as recrystallization or column chromatography.

Exemplary acids usable to convert the pyrroloazepine derivatives (I) to their salts include inorganic acids such as hydrochloric acid, nitric acid, sulfuric acid, phosphoric acid and hydrobromic acid; and organic acids such as maleic acid, fumaric acid, tartaric acid, oxalic acid, lactic acid, citric acid, acetic acid, methanesulfonic acid, p-toluenesulfonic acid, adipic acid, palmitic acid and tannic acid.

The pyrroloazepine derivatives (I) and their salts according to the present invention, which are obtained as described above, have anti-serotonin action and anti-$a_1$ action as will be demonstrated later by tests. Further, as a result of a toxicity test, they have been found to have a high degree of safety. The compounds according to the present invention can therefore be used as therapeutics for circulatory diseases such as hypertension and congestive heart failure.

When the pyrroloazepine derivatives (I) and their salts according to this invention are used as drugs, they can be administered in an effective dose as they are. As an alternative, they can also be formulated into various preparation forms by known methods and then administered.

Exemplary preparation forms as drugs include orally administering preparation forms such as tablets, powders, granules, capsules and syrups as well as parenterally administering preparation forms such as injections and suppositories. Whichever preparation form is used, a known liquid or solid extender or carrier usable for the formulation of the preparation form can be employed.

Examples of such extender or carrier include polyvinylpyrrolidone, arabic gum, gelatin, sorbit, cyclodextrin, tragacanth, magnesium stearate, talc, polyethylene glycol, polyvinyl alcohol, silica, lactose, crystalline cellulose, sugar, starch, calcium phosphate, vegetable oil, carboxymethylcellulose, sodium laurylsulfate, water, ethanol, glycerin, mannitol, and syrup.

When the compounds according to the present invention are used as drugs, their dose varies depending on the administration purpose, the age, body weight and conditions of the patient to be administered, etc. In oral administration, the daily dose may generally be about 0.1–1,000 mg.

The present invention will next be described in further detail by the following referential examples, examples and tests.

REFERENTIAL EXAMPLE 1

Synthesis of ethyl 3-(N-methyl-2-pyrrolecarboxamido)propionate (Compound No. 1)

A solution of 50.0 g (450 mmol) of pyrrole-2-carboxylic acid and 64.9 g (495 mmol) of ethyl 3-(methylamino)-propionate in 200 ml of DMF was cooled to 0° C., followed by the addition of a solution of 80.8 g (495 mmol) of diethyl cyanophosphate in 100 ml of dimethylformamide (DMF) under stirring. After a solution of 50.1 g (495 mmol) of triethylamine in 100 ml of DMF was added dropwise at the same temperature over 1 hour, the resultant mixture was stirred for 18 hours at room temperature.

To an oil obtained by concentrating the reaction mixture under reduced pressure, 1200 ml of a mixed solvent of ethyl acetate and benzene (3:1 v/v) were added. The organic layer was washed successively with a saturated aqueous solution of potassium carbonate, water, 5% hydrochloric acid solution, water (twice) and saturated saline, followed by drying over anhydrous sodium sulfate. To an oil obtained by distilling off the solvent under reduced pressure, isopropyl ether (200 ml) and hexane (1000 ml) were added. After the resultant mixture was shaken, it was allowed to stand for one day.

Precipitated crystals were collected by filtration and then dried under reduced pressure, whereby 87.5 g of the title compound were obtained as colorless powdery crystals (yield: 87%).

Although this compound was sufficiently pure, it can be recrystallized from isopropyl ether as needed. Appearance: Colorless prism crystals. Melting point: 57.0°–58.0° C.

REFERENTIAL EXAMPLE 2

Compound No. 2 was obtained by using ethyl 3-(benzylamino)propionate in place of ethyl 3-(methylamino)propionate in the procedure described in Referential Example 1. (Compound No. 2)

Ethyl 3-(N-benzyl-2-pyrrolecarboxamido)propionate

REFERENTIAL EXAMPLE 3

Synthesis of
3-(N-methyl-2-pyrrolecarboxamido)propionic acid
(Compound No. 3)

A mixture of 37.00 g (165 mmol) of Compound No. 1 obtained in Referential Example 1, 413 ml (826 mmol) of a 2N aqueous solution of sodium hydroxide and 20 ml of ethanol was stirred for 4 hours at room temperature. The reaction mixture was cooled, and 80 ml of concentrated hydrochloric acid were added under stirring, followed by further stirring. Precipitated crystals were then collected by filtration.

The filtrate was saturated with sodium chloride, followed by extraction with ethyl acetate. The extract was dried over anhydrous sodium sulfate, followed by concentration under reduced pressure, whereby crystals were obtained.

Both the crystals were combined and recrystallized from ethyl acetate, whereby 27.69 g of the title compound were obtained (yield: 86%). Appearance: Colorless prism crystals. Melting point: 125.0°–127.0° C.

REFERENTIAL EXAMPLE 4

Compound No. 4 was obtained by using Compound No. 2 in place of Compound No. 1 in the procedure described in Referential Example 3. (Compound No. 4)

3-(N-benzyl-2-pyrrolecarboxamido)propionic acid

REFERENTIAL EXAMPLE 5

Synthesis of
7-methyl-6,7-dihydropyrrolo[2,3-c]azepine-4,8(1H,5H)-dione (Compound No. 5)

A mixture of 7.00 g (35.68 mmol) of Compound No. 3 obtained in Referential Example 3 and 250 g of polyphosphoric acid (about 80%) was vigorously stirred for 30 minutes by a mechanical stirrer over an oil bath maintained at 100° C.

The reaction mixture was poured into 700 ml of ice water, followed by extraction with chloroform. The organic layer was washed with saturated saline (twice) and then dried over anhydrous sodium sulfate.

The solvent was distilled off under reduced pressure, whereby 5.58 g of the title compound were obtained as pale brown crystals (yield: 88%).

Although this compound was sufficiently pure, it can be recrystallized from chloroform-isopropyl ether as needed.

REFERENTIAL EXAMPLE 6

Compound No. 6 was obtained by using Compound No. 4 in place of Compound No. 3 in the procedure described in Referential Example 5. (Compound No. 6)

7-Benzyl-6,7-dihydropyrrolo[2,3-c]azepine-4,8(1H,5H)-dione

REFERENTIAL EXAMPLE 7

Synthesis of
7-benzyl-1-(4-bromobutyl)-6,7-dihydropyrrolo[2,3-c]azepine-4,8(1H,5H)-dione (Compound No. 7)

A suspension of 0.76 g (3 mmol) of Compound No. 6 obtained in Referential Example 6, 3.24 g (15 mmol) of 1,4-dibromobutane and 2.07 g (15 mmol) of potassium carbonate in 50 ml of DMF was stirred at 80° C. for 3 hours. The reaction mixture was added with 200 ml of a mixed solvent of ethyl acetate and benzene (2:1 v/v), washed with a 10% aqueous solution of citric acid, water (thrice) and saturated saline, and then dried over anhydrous sodium sulfate. The solvent was distilled off under reduced pressure. The residue was purified by chromatography on a silica gel column in which silica gel "Art. 9385" (product of Merck & Co.; the same silica gel was also used in the subsequent examples) was used as silica gel (eluent: 1:3 mixed solvent of ethyl acetate and benzene), whereby 0.83 g of the title compound was obtained (yield: 71%).

REFERENTIAL EXAMPLE 8

Compound Nos. 8, 9, 10 and 11 were obtained by using 1,2-dibromoethane, 1,3-dibromopropane, 1,5-dibromopentane and 1,8-dibromooctane in place of 1,4-dibromobutane, respectively, in the procedure of Referential Example 7. Further, Compound Nos. 12, 13 and 14 were obtained from the combinations of Compound No. 5 and 1,4-dichlorobutane, 1,4-dibromobutane and 1,5-dibromopentane, respectively. (Compound No. 8)

7-Benzyl-1-(2-bromoethyl)-6,7-dihydropyrrolo[2,3-c]azepine-4,8(1H,5H)-dione (Compound No. 9)

7-Benzyl-1-(3-bromopropyl)-6,7-dihydropyrrolo[2,3-c]azepine-4,8(1H,5H)-dione (Compound No. 10)

7-Benzyl-1-(5-bromopentyl)-6,7-dihydropyrrolo[2,3-c]azepine-4,8(1H,5H)-dione (Compound No. 11)

7-Benzyl-1-(8-bromooctyl)-6,7-dihydropyrrolo[2,3-c]azepine-4,8(1H,5H)-dione (Compound No. 12)

1-(4-Chlorobutyl)-7-methyl-6,7-dihydropyrrolo[2,3-c]azepine-4,8(1H,5H)-dione (Compound No. 13)

1-(4-Bromobutyl)-7-methyl-6,7-dihydropyrrolo[2,3-c]azepine-4,8(1H,5H)-dione (Compound No. 14)

1-(5-Bromopentyl)-7-methyl-6,7-dihydropyrrolo[2,3-c]azepine-4,8(1H,5H)-dione

REFERENTIAL EXAMPLE 9

Synthesis of 1-(4-chlorobutyl)-4-hydroxyimino-7-methyl-4,5,6,7-tetrahydropyrrolo[2,3-c]azepin-8(1H)-one (Compound No. 15)

A solution of 4,031 g (15 mmol) of Compound No. 12 obtained in Referential Example 8 and 5.212 g (75 mmol) of hydroxylamine hydrochloride in 90 ml of pyridine was stirred for 18 hours at room temperature.

After the reaction mixture was concentrated under reduced pressure, toluene was added, followed by concentration again under reduced pressure. The residue was added with 200 ml of a 10% aqueous solution of citric acid and then extracted with chloroform. The extract was washed with saturated saline and then dried over anhydrous sodium sulfate. The solvent was distilled off under reduced pressure and the resultant oil was purified by chromatography on a silica gel column (eluent: 7.5% methanol-chloroform), whereby 3.84 g of a colorless oil were obtained (yield: 90%). The oil was crystallized when treated with isopropyl ether.

Although this compound is sufficiently pure, it can be recrystallized from ethyl acetate if necessary.

REFERENTIAL EXAMPLE 10

Synthesis of 7-benzyl-1-(2,3-epoxypropyl)-6,7-dihydropyrrolo[2,3-c]azepine-4,8(1H,5H)-dione (Compound 16)

A suspension of 509 mg (2 mmol) of Compound No. 6 obtained in Referential Example 6, 822 mg (6 mmol) of epibromohydrin and 829 mg (6 mmol) of potassium carbonate in 50 ml of acetonitrile was refluxed for 14 hours. After the reaction mixture was filtered, the solvent was distilled off under reduced pressure. The residue was added with ethyl acetate, followed by washing with saturated saline. After the organic layer was dried over anhydrous sodium sulfate, the solvent was distilled off under reduced pressure. The residue was purified by chromatography on a silica gel column (eluent: 1:1 mixed solvent of ethyl acetate and hexane), whereby 520 mg of the title compound were obtained (yield: 84%).

EXAMPLE 1

Synthesis of 7-benzyl-1-[4-(4-phenylpiperazin-1-yl)butyl]-6,7-dihydropyrrolo[2,3-c]azepine-4,8-(1H,5H)-dione (Compound No. 17)

A suspension of 389 mg (1 mmol) of Compound No. 7, 811 mg (5 mmol) of 1-phenylpiperazine and 691 mg (5 mmol) of potassium carbonate in 30 ml of DMF was stirred at 80° C. for 4 hours.

After cooling, the reaction mixture was added with a mixed solvent of ethyl acetate and benzene (3:1 v/v), followed by washing with water (thrice) and then with saturated saline. The organic layer was thereafter dried over anhydrous sodium sulfate. The solvent was then distilled off under reduced pressure. The residue was purified by chromatography on a silica gel column (eluent: ethyl acetate), whereby 400 mg of the title compound were obtained (yield: 85%).

EXAMPLE 2

Compound Nos. 18, 19, 20, 21, 22 and 23 were obtained by using Compound Nos. 8, 9, 10, 11, 13 and 14 in place of Compound No. 7 in the procedure of Example 1. (Compound No. 18)

7-Benzyl-1-[2-(4-phenylpiperazin-1-yl)ethyl]-6,7-dihydropyrrolo[2,3-c]azepine-4,8(1H,5H)-dione (Compound No. 19)

7-Benzyl-1-[3-(4-phenylpiperazin-1-yl)propyl]-6,7-dihydropyrrolo[2,3-c]azepine-4,8(1H,5H)-dione (Compound No. 20)

7-Benzyl-1-[5-(4-phenylpiperazin-1-yl)pentyl]6,7-dihydropyrrolo[2,3-c]azepine-4,8(1H,5H)-dione (Compound No. 21)

7-Benzyl-1-[8-(4-phenylpiperazin-1-yl)octyl]-6,7-dihydropyrrolo[2,3-c]azepine-4,8(1H,5H)-dione (Compound No. 22)

7-Methyl-1-[4-(4-phenylpiperazin-1-yl)butyl]-6,7-dihydropyrrolo[2,3-c]azepine-4,8(1H,5H)-dione (Compound No. 23)

7-Methyl-1-[5-(4-phenylpiperazin-1-yl)pentyl]-6,7-dihydropyrrolo[2,3-c]azepine-4,8(1H,5H)-dione

EXAMPLE 3

Synthesis of 4-hydroxy-7-methyl-1-[4-(4-phenylpiperazin-1-yl)butyl]-4,5,6,7-tetrahydropyrrolo[2,3-c]azepin-8(1H)-one (Compound No. 24)

In 30 ml of methanol, 592 mg (1.5 mmol) of Compound No. 22, which had been obtained in Example 2, were dissolved. To the resulting solution, 1.50 g (39.7 mmol) of sodium borohydride were added slowly under cooling and stirring, followed by stirring at room temperature for 2 hours. The reaction mixture was concentrated under reduced pressure, followed by the addition of ethyl acetate. The organic layer was washed thrice with a saturated aqueous solution of potassium chloride, and then dried over anhydrous sodium sulfate. The solvent was distilled off under reduced pressure and the residue was purified by chromatography on a silica gel column (eluent: ethyl acetate→8% methanol-chloroform), whereby 530 mg of the title compound were obtained (yield: 89%).

EXAMPLE 4

Synthesis of 7-methyl-1-[4-(4-phenylpiperazin-1-yl)butyl]-6,7-dihydropyrrolo[2,3-c]azepin-8(1H)-one (Compound No. 25)

In 20 ml of dichloromethane, 119 mg (0.3 mmol) of Compound No. 24, which had been obtained in Example 3, and 2.02 g (20 mmol) of triethylamine were dissolved. To the resulting solution, a solution of 344 mg (3 mmol) of methanesulfonyl chloride in 5 ml of dichloromethane was added slowly under cooling and stirring, followed by stirring at room temperature for 3 hours. The reaction mixture was added with 300 ml of ethyl acetate. The organic layer was washed successively with a saturated aqueous solution of potassium carbonate (twice), water (twice) and saturated saline, and then dried over anhydrous sodium sulfate. The solvent was distilled off under reduced pressure and the residue was purified by chromatography on a silica gel column (eluent: 5% methanol-chloroform), whereby 89 mg of the title compound were obtained (yield: 78%).

EXAMPLE 5

Synthesis of
4-hydroxyimino-7-methyl-1-[5-(4-phenylpiperazin-1-yl)pentyl]-4,5,6,7-tetrahydropyrrolo[2,3-c]azepin-8(1H)-one (Compound No. 26)

A solution of 163 mg (0.4 mmol) of Compound No. 23 obtained in Example 2 and 139 mg (2 mmol) of hydroxylamine hydrochloride in 20 ml of pyridine was stirred at 70° C. for 2 hours. After the reaction mixture was concentrated under reduced pressure, the residue was added with a saturated aqueous solution of potassium carbonate and then extracted with chloroform. The organic layer was washed with saturated saline and then dried over anhydrous sodium sulfate. The solvent was distilled off under reduced pressure. The residue was purified by chromatography on a silica gel column (eluent: 5% methanol-chloroform), whereby 160 mg of the title compound were obtained (yield: 95%).

EXAMPLE 6

Compound No. 27 was obtained using Compound No. 22 in place of Compound No. 23 in the procedure of Example 5. (Compound No. 27)

4-Hydroxyimino-7-methyl-1-[4-(4-phenylpiperazin-1-yl)butyl]-4,5,6,7-tetrahydropyrrolo[2,3-c]azepin-8(1H)-one

EXAMPLE 7

Synthesis of
7-methyl-1-[4-[4-(4-fluorophenyl)piperazin-1-yl]butyl]-6,7-dihydropyrrolo[2,3-c]azepine-4,8(1H,5H)-dione (Compound No. 28)

In 70 ml of DMF, 806 mg (3 mmol) of Compound No. 13 and 2.16 g (12 mmol) of 1-(4-fluorophenyl)piperazine were dissolved. The resulting solution was added with 4.50 g (30 mmol) of sodium iodide, followed by stirring at 80° C. for 6 hours.

The reaction mixture was then post-treated and purified as in Example 1, whereby 1.19 g of the title compound were obtained (yield: 96%).

EXAMPLE 8

Compound No. 29 was obtained using Compound No. 28 in place of Compound No. 23 in the procedure of Example 5. (Compound No. 29)

4-Hydroxyimino-7-methyl-1-[4-[4-(4-fluorophenyl)-piperazin-1-yl]butyl]-4,5,6,7-tetrahydropyrrolo[2,3-c]azepin-8(1H)-one

EXAMPLE 9

Synthesis of
1-[4-[4-(3-chlorophenyl)piperazin-1-yl]butyl]-7-methyl-6,7-dihydropyrrolo[2,3-c]azepine-4,8(1H,5H)-dione (Compound No. 30)

A suspension of 109 mg (0.39 mmol) of Compound No. 12, 108 mg (0.46 mmol) of 1-(3-chlorophenyl)piperazine hydrochloride, 117 mg (0.85 mmol) of potassium carbonate and 54 mg (0.39 mmol) of sodium iodide in 5 ml of DMF was stirred at 80° C. for 12 hours. The reaction mixture was post-treated and purified as in Example 1, whereby 144 mg of the title compound were obtained (yield: 86%).

EXAMPLE 10

Compound No. 31 was obtained using Compound No. 15 in place of Compound No. 12 in the procedure of Example 9. Further, Compound Nos. 32 and 33 were obtained using Compound No. 12 and 1-(4-chlorophenyl)piperazine hydrochloride and Compound No. 15 and 1-(4-chlorophenyl)piperazine hydrochloride, respectively. (Compound No. 31)

1-[4-[4-(3-Chlorophenyl)piperazin-1-yl]butyl]-4-hydroxyimino-7-methyl-4,5,6,7-tetrahydropyrrolo[2,3-c]azepin-8(1H)-one (Compound No. 32)

1-[4-[4-(4-Chlorophenyl)piperazin-1-yl]butyl]-7-methyl-6,7-dihydropyrrolo[2,3-c]azepine-4,8(1H,5H)-dione (Compound No. 33)

1-[4-[4-(4-Chlorophenyl)piperazin-1-yl]butyl]-4-hydroxyimino-7-methyl-4,5,6,7-tetrahydropyrrolo[2,3-c]azepin-8(1H)-one

EXAMPLE 11

Synthesis of
1-[4-[4-(2-methoxyphenyl)piperazin-1-yl]butyl]-7-methyl-6,7-dihydropyrrolo[2,3-c]azepine-4,8(1H,5H)-dione (Compound No. 34)

A suspension of 313 mg (1 mmol) of Compound No. 13, 385 mg (2 mmol) of 1-(2-methoxyphenyl)piperazine and 276 mg (2 mmol) of potassium carbonate in 10 ml of DMF was stirred at 80° C. for 16 hours. The reaction mixture was added with a mixed solvent of ethyl acetate and benzene (3:1 v/v). The organic layer was washed with a saturated aqueous solution of potassium carbonate, water (twice) and saturated saline and then dried over anhydrous sodium sulfate. The solvent was distilled off under reduced pressure. The residue was purified by chromatography on a silica gel column (eluent: 3% methanol-chloroform), whereby 390 mg of the title compound were obtained (yield: 92%).

EXAMPLE 12

Compound Nos. 35 and 36 were obtained using Compound Nos. 14 and 10, respectively, in place of Compound No. 13 in the procedure of Example 11. (Compound No. 35)

1-[5-[4-(2-Methoxyphenyl)piperazin-1-yl]pentyl]-7-methyl-6,7-dihydropyrrolo[2,3-c]azepine-4,8(1H,5H)-dione (Compound No. 36)

7-Benzyl-1-[5-[4-(2-methoxyphenyl)piperazin-1-yl]pentyl]-6,7-dihydropyrrolo[2,3-c]azepine-4,8(1H,5H)-dione

EXAMPLE 13

Synthesis of
7-methyl-1-[4-[4-(2-pyrimidinyl)piperazin-1-yl]butyl]-6,7-dihydropyrrolo[2,3-c]azepine-4,8(1H,5H)-dione (Compound No. 37)

A suspension of 939 mg (3.49 mmol) of Compound No. 12, 2.85 g (12.0 mmol) of 1-(2-pyrimidinyl)piperazine dihydrochloride, 4.98 g (36.0 mmol) of potassium carbonate and 1.05 g (7.0 mmol) of sodium iodide in 50 ml of DMF was stirred at 80° C. for 16 hours. The reaction mixture was post-treated and purified as in Example 1, whereby 1.15 g of the title compound were obtained (yield: 83%).

EXAMPLE 14

Synthesis of
4-hydroxyimino-7-methyl-1-[4-[4-(2-pyrimidinyl)piperazin-1-yl]butyl]-4,5,6,7-tetrahydropyrrolo[2,3-c]azepin-8(1H)-one (Compound No. 38)

A suspension of 397 mg (1.0 mmol) of Compound No. 37, 139 mg (2.0 mmol) of hydroxylamine hydrochloride and 164 mg (2.0 mmol) of sodium acetate in 30 ml of methanol was refluxed for 16 hours. The reaction mixture was concentrated under reduced pressure. The residue was added with a half-saturated aqueous solution of potassium carbonate and then extracted with chloroform (thrice). The organic layer was washed with saturated saline and then dried over anhydrous sodium sulfate. The solvent was distilled off under reduced pressure. The residue was purified by chromatography on a silica gel column (eluent: 5% methanol-chloroform), whereby 372 mg of the title compound were obtained (yield: 91%).

EXAMPLE 15

Compound Nos. 39, 40, 41, 42, 43, 44, 45, 46 and 47 were obtained using 1-(2-pyridyl)piperazine, 1-ethoxycarbonylpiperazine, 1-benzylpiperazine, 1-benzoylpiperazine, 1-(4-benzyloxybenzoyl)piperazine, 1-(2-furoyl)piperazine, 1-(diphenylmethyl)piperazine, 1-cinnamylpiperazine and 1-(1,4-benzodioxan-2-ylmethyl)piperazine, respectively, in place of 1-(2-methoxyphenyl)piperazine in the procedure of Example 11. (Compound No. 39)

7-Methyl-1-[4-[4-(2-pyridyl)piperazin-1-yl]butyl]-6,7-dihydropyrrolo[2,3-c]azepine-4,8-(1H,5H)-dione (Compound No. 40)

1-[4-(4-Ethoxycarbonylpiperazin-1-yl)butyl]-7-methyl-6,7-dihydropyrrolo[2,3-c]azepine-4,8(1H,5H)-dione (Compound No. 41)

1-[4-(4-Benzylpiperazin-1-yl)butyl]-7-methyl-6,7-dihydropyrrolo[2,3-c]azepine-4,8(1H,5H)-dione (Compound No. 42)

1-[4-(4-Benzoylpiperazin-1-yl)butyl]-7-methyl-6,7-dihydropyrrolo[2,3-c]azepine-4,8(1H,5H)-dione (Compound No. 43)

1-[4-[4-(4-Benzyloxyphenylcarbonyl)piperazin-1-yl]butyl]-7-methyl-6,7-dihydropyrrolo[2,3-c]azepine-4,8(1H,5H)-dione (Compound No. 44)

1-[4-[4-(2-Furoyl)piperazin-1-yl]butyl]-7-methyl-6,7-dihydropyrrolo[2,3-c]azepine-4,8(1H,5H)-dione (Compound No. 45)

1-[4-(4-Diphenylmethylpiperazin-1-yl)butyl]-7-methyl-6,7-dihydropyrrolo[2,3-c]azepine-4,8(1H,5H)-dione (Compound No. 46)

1-[4-(4-Cinnamylpiperazin-1-yl)butyl]-7-methyl-6,7-dihydropyrrolo[2,3-c]azepine-4,8(1H,5H)-dione (Compound No. 47)

1-[4-[4-(1,4-benzodioxan-2-ylmethyl)piperazin-1-yl]butyl]-7-methyl-6,7-dihydropyrrolo[2,3-c]azepine-4,8(1H,5H)-dione

EXAMPLE 16

Synthesis of
1-[4-[4-(4-hydroxyphenyl)piperazin-1-yl]butyl]-7-methyl-6,7-dihydropyrrolo[2,3-c]azepine-4,8(1H,5H)-dione (Compound No. 48)

In 2 ml of methanol, 23 mg (0.046 mmol) of Compound No. 43, which had been obtained in Example 15, were dissolved, followed by the addition of 16 mg of 5% palladium-carbon. After excess hydrogen was introduced into the system, vigorous stirring was conducted at room temperature for 15 hours. The reaction mixture was filtered to remove any insoluble matter and the solvent was distilled off under reduced pressure, whereby 13 mg of the title compound were obtained (yield: 65%).

EXAMPLE 17

Synthesis of
1-[4-(1-imidazolyl)butyl]-7-methyl-6,7-dihydropyrrolo[2,3-c]azepine-4,8(1H,5H)-dione (Compound No. 49)

To a suspension of 40 mg (1 mmol) of 60% sodium hydride in 10 ml of DMF, a solution of 68 mg (1 mmol) of imidazole in 5 ml of DMF was added dropwise under cooling and stirring, followed by stirring at room temperature for one hour. To the reaction mixture, a solution of 313 mg (1 mmol) of Compound No. 13 in 5 ml of DMF was added, followed by stirring at 80° C. for 3 hours. The reaction mixture was post-treated and purified as in Example 1, whereby 174 mg of the title compound were obtained (yield: 58%).

EXAMPLE 18

Synthesis of
7-benzyl-1-[2-(dimethylamino)ethyl]-6,7-dihydropyrrolo[2,3-c]azepine-4,8(1H,5H)-dione (Compound No. 50)

A suspension of 254 mg (1 mmol) of Compound No. 6, 720 mg (5 mmol) of 2-(dimethylamino)ethylchloride hydrochloride and 1.38 g (10 mmol) of potassium carbonate in 30 ml of DMF was heated at 80° C. for 3 hours. The reaction mixture was post-treated and purified as in Example 1, whereby 250 mg of the title compound were obtained (yield: 77%).

EXAMPLE 19

Synthesis of
7-benzyl-1-[[2-hydroxy-3-(1,1-dimethylethylamino)]-propyl]-6,7-dihydropyrrolo[2,3-c]azepine-4,8(1H,5H)-dione (Compound No. 51)

A solution of 155 mg (0.5 mmol) of Compound No. 16 and 1.00 g (13.7 mmol) of tert-butylamine in 20 ml of ethanol was refluxed for 48 hours. The reaction mixture was concentrated under reduced pressure. The residue was purified by chromatography on a silica gel column (eluent: 5% methanol-chloroform), whereby 110 mg of the title compound were obtained (yield: 57%).

EXAMPLE 20

Synthesis of
7-benzyl-1-[[2-hydroxy-3-(4-phenylpiperazin-1-yl)]propyl]-6,7-dihydropyrrolo[2,3-c]azepine-4,8(1H,5H)-dione (Compound No. 52)

A solution of 155 mg (0.5 mmol) of Compound No. 16 and 243 mg (1.5 mmol) of 1-phenylpiperazine in 30 ml of toluene was refluxed for 48 hours. The reaction mixture was post-treated and purified as in Example 17, whereby 180 mg of the title compound were obtained (yield: 76%).

EXAMPLE 21

Compound Nos. 53 and 54 were obtained using compound No. 7 and 2-phenoxyethylamine and Compound No. 13 and 2-phenoxyethylamine, respectively, in the procedure of Example 1. (Compound No. 53)

7-Benzyl-1-[4-[N-(2-phenoxyethyl)amino]butyl]-6,7-dihydropyrrolo[2,3-c]azepine-4,8(1H,5H)-dione (Compound No. 54)

7-Methyl-1-[4-[N-(2-phenoxyethyl)amino]butyl]-6,7-dihydropyrrolo[2,3-c]azepine-4,8(1H,5H)-dione

EXAMPLE 22

Synthesis of 4-hydroxyimino-7-methyl-1-[4-(2-phenoxyethylamino)-butyl]-4,5,6,7-tetrahydropyrrolo[2,3-c]azepin-8(1H)-one (Compound No. 55)

A suspension of 1.14 g (4 mmol) of Compound No. 15, 549 mg (4 mmol) of 2-phenoxyethylamine, 672 mg (8 mmol) of sodium hydrogencarbonate and 1.20 g (8 mmol) of sodium iodide in 50 ml of acetonitrile was refluxed for 20 hours. The reaction mixture was post-treated and purified as in Example 14, whereby 636 mg of the title compound were obtained (yield: 41%).

EXAMPLE 23

Compound Nos. 56 and 57 were obtained using Compound No. 13 and 3-phenylpropylamine and Compound No. 13 and N-propyl-2-(8-hydroxy-1,2,3,4-tetrahydronaphthyl)amine, respectively, in the procedure of Example 1. (Compound No. 56)

7-Methyl-1-[4-[N-(3-phenylpropyl)amino]butyl]-6,7-dihydropyrrolo[2,3-c]azepine-4,8(1H,5H)-dione (Compound No. 57)

7-Methyl-1-[4-[N-propyl-2-(8-hydroxy-1,2,3,4-tetrahydronaphthyl)amino]butyl]-6,7-dihydropyrrolo[2,3-c]azepine-4,8(1H,5H)-dione Data of physical properties of the compounds obtained in the above examples are summarized in Table 1.

TABLE 1

| Comp'd No. | Property Melting point (recrystallization solvent) | NMR*1 (δ ppm 270 MHz) | IR*2 (cm$^{-1}$) | Yield (%) | Structural formula |
|---|---|---|---|---|---|
| 5 | Colorless needle crystals 175.0–177.0° C. (chloroform-diisopropyl ether) | 2.89(2H, m), 3.27(3H, s), 3.73(2H, m) 6.77(1H, t, J=2.6Hz), 6.94(1H, t, J=2.6Hz), 10.84(1H, br.) | 3425, 2450, 1665 1620, 1480, 1400 1365, 1145, 1080 945 | 88 | ![structure with N-CH$_3$, NH] |
| 6 | Colorless needle crystals 176.0–179.0° C. (chloroform-hexane) | 2.74(2H, m), 3.67(2H, m), 4.87(2H, s) 6.77(1H, m), 6.89(1H, t, J=2.6Hz) 7.22–7.44(5H, m), 11.24(1H, br.) | 3420, 1665, 1620 1480, 1365, 1075 1025 | 47 | ![structure with N-CH$_2$Ph, NH] |
| 7 | Colorless oil | 1.75–2.08(4H, m), 2.62(2H, m) 3.38(2H, t, J=6.3Hz), 3.65(2H, m) 4.43(2H, t, J=6.9Hz), 4.80(2H, s) 6.65(1H, d, J=2.6Hz), 6.82(1H, d, J=2.6Hz) 7.20–7.45(5H, m) | 2900, 1655, 1625 1475, 1370, 980 | 63 | ![structure with N-CH$_2$Ph, N-(CH$_2$)$_4$Br] |
| 8 | Pale yellow oil | 2.64(2H, dd, J=6.6Hz, 4.0Hz), 3.67(2H, t), 3.78(2H, t, J=5.9Hz), 4.75(2H, t, J=5.9Hz), 4.80(2H, s), 6.68(1H, d, J=3.0Hz), 6.91(1H, d, J=3.0Hz), 7.18–7.44(5H, m) | (film) 1662, 1628, 1528, 1483, 1434, 1373, 1284, 1243, 1210 | 30 | ![structure with N-CH$_2$Ph, N-(CH$_2$)$_2$Br] |

TABLE 1-continued

| Comp'd No. | Property Melting point (recrystallization solvent) | NMR*1 (δ ppm 270 MHz) | IR*2 (cm⁻¹) | Yield (%) | Structural formula |
|---|---|---|---|---|---|
| 9 | Colorless oil | 2.41(2H, m), 2.62(2H, dd, J=6.0Hz, 4.0Hz), 3.38(2H, t, J=6.6Hz), 3.63(2H, m), 4.53(2H, t, J=7.3Hz), 4.78(2H, s), 6.67(1H, d, J=2.7Hz), 6.89(1H, d, J=2.7Hz), 7.17-7.45(5H, m) | (film) 1661, 1634, 1526, 1485, 1435, 1373, 1244, 1209 | 35 | (structure with N-CH₂Ph and (CH₂)₃Br) |
| 10 | Pale yellow oil | 1.50(2H, m), 1.78-1.97(4H, m), 2.62(2H, dd, J=5.9Hz, 4.0Hz), 3.39(2H, t, J=6.6Hz), 3.66(2H, m), 4.39(2H, t, J=7.3Hz), 4.80(2H, s), 6.65(1H, d, J=2.7Hz), 6.82(1H, d, J=2.7Hz), 7.22-7.44(5H, m) | (film) 2937, 1661, 1632, 1485, 1433, 1374, 1241, 1208 | 47 | (structure with N-CH₂Ph and (CH₂)₅Br) |
| 11 | Yellow oil | 1.18-1.55(8H, m), 1.73-1.93(4H, m), 2.62(2H, dd, J=5.9Hz, 4.0Hz), 3.39(2H, t, J=6.6Hz), 3.64(2H, m), 4.38(2H, t, J=7.3Hz), 4.80(2H, s), 6.64(1H, d, J=3.3Hz), 6.81(1H, d, J=3.3Hz), 7.22-7.43(5H, m) | (film) 2929, 2855, 1632, 1526, 1485, 1474, 1242, 1208, 1144 | 51 | (structure with N-CH₂Ph and (CH₂)₈Br) |
| 12 | Colorless prism crystals 59.0-60.5° C. (ethyl acetate-hexane) | 1.80(2H, m), 1.98(2H, m), 2.79(2H, m), 3.21(3H, s), 3.54(2H, t, J=6.6Hz), 3.71(2H, m), 4.36(2H, t, J=7.2Hz), 6.65(1H, d, J=2.6Hz), 6.80(1H, d, J=2.6Hz) | 2945, 1660, 1635, 1520, 1485, 1435, 1395, 1375, 1325, 1295, 1110, 1075, 910 | 97 | (structure with N-CH₃ and (CH₂)₄Cl) |

TABLE 1-continued

| Comp'd No. | Property Melting point (recrystalli- zation solvent) | NMR*1 (δ ppm 270 MHz) | IR*2 (cm−1) | Yield (%) | Structural formula |
|---|---|---|---|---|---|
| 13 | Colorless solid | 1.80–2.07(4H, m), 2.79(2H, m), 3.21(3H, s) 3.40(2H, t, J=6.3Hz), 3.72(2H, m) 4.36(2H, t, J=7.0Hz), 6.65(1H, d, J=2.6Hz) 6.80(1H, d, J=2.6Hz) | 2925, 1655, 1630 1480, 1395, 1320 1110, 1085, 905 | 43 | (structure with N-CH₃, (CH₂)₄Br) |
| 14 | Pale yellow oil | 1.48(2H, m), 1.75–2.00(4H, m), 2.79(2H, m), 3.21(3H, s), 3.40(2H, t, J=6.6Hz), 3.71(2H, m), 4.33(2H, t, J=7.3Hz), 6.64(1H, d, J=3.0Hz), 6.79(1H, d, J=3.0Hz) | 2920, 1655, 1620, 1465, 1395, 1100, 900 | 64 | (structure with N-CH₃, (CH₂)₅Br) |
| 15 | Colorless needle crystals 113.0–114.0° C. (ethyl acetate) | 1.77(2H, m), 1.93(2H, m), 2.98(2H, m) 3.13(3H, s), 3.51(2H, t, J=6.3Hz) 3.58(2H, m), 4.31(2H, t, J=6.9Hz) 6.39(1H, d, J=2.6Hz), 6.76(1H, d, J=2.6Hz) 9.33(1H, br.s) | 3555, 3250, 2930 1620, 1475, 1395 1360, 960, 940 | 90 | (structure with NOH, N-CH₃, (CH₂)₄Cl) |
| 16 | Colorless oil | 2.48(1H, dd, J=4.6Hz, 2.6Hz), 2.64(2H, dd, J=6.6Hz, 4.4Hz), 2.84(1H, t, J=2.6Hz), 3.45(1H, m), 3.66(2H, m), 4.16(1H, dd, J=14.5Hz, 5.9Hz), 4.78(1H, d, J=15.2Hz), 4.81(1H, d, J=15.2Hz), 4.98(1H, dd, J=14.5Hz, 2.0Hz), 6.67(1H, d, J=2.6Hz), 6.89(1H, d, J=2.6Hz), 7.23–7.45(5H, m) | (film) 1632, 1529, 1484, 1435, 1374, 1244, 1210, 1142, 1079 | 82 | (structure with N-CH₂Ph, CH₂CH-CH₂-O) |

TABLE 1-continued

| Comp'd No. | Property Melting point (recrystallization solvent) | NMR*1 (δ ppm 270 MHz) | IR*2 (cm⁻¹) | Yield (%) | Structural formula |
|---|---|---|---|---|---|
| 17 | Colorless oil | 1.57(2H, m), 1.89(2H, m), 2.42(2H, t, J=7.3Hz), 2.47-2.77(6H, m), 3.18(4H, m), 3.65(2H, m), 4.42(2H, t, J=7.3Hz), 4.80(2H, s), 6.65(1H, d, J=3.0Hz), 6.75-7.03(4H, m), 7.14-7.48(7H, m) | 2940, 2815, 1660 1630, 1595, 1485, 1260, 1025 | 85 | (structure with (CH$_2$)$_4$ linker) |
| 18 | Colorless oil | 2.51-2.73(6H, m), 2.80(2H, t, J=6.6Hz), 3.14(4H, m), 3.67(2H, m), 4.55(2H, t, J=6.6Hz), 4.79(2H, s), 6.64(1H, d, J=2.7Hz), 6.80-7.00(4H, m), 7.19-7.45(7H, m) | 2945, 2820, 1655, 1610, 1595, 1480, 1260, 1140, 1020 | 27 | (structure with (CH$_2$)$_2$ linker) |
| 19 | Pale yellow oil | 2.04(2H, m), 2.40(2H, t, J=6.9Hz), 2.48-2.70(6H, m), 3.10-3.29(4H, m), 3.65(2H, m), 4.47(2H, t, J=6.9Hz), 4.80(2H, s), 6.65(1H, d, J=2.7Hz), 6.80-7.01(4H, m), 7.18-7.42(7H, m) | 2950, 1630, 1480, 1395, 1250, 1095 | 93 | (structure with (CH$_2$)$_3$ linker) |

TABLE 1-continued

| Comp'd No. | Property Melting point (recrystallization solvent) | NMR*1 (δ ppm 270 MHz) | IR*2 (cm$^{-1}$) | Yield (%) | Structural formula |
|---|---|---|---|---|---|
| 20 | Pale yellow oil | 1.38(2H, m), 1.58(2H, m), 1.88(2H, m), 2.38(2H, m), 2.46–2.71(6H, m), 3.20(4H, m), 3.65(2H, m), 4.39(2H, t, J=7.3Hz), 4.80(2H, s), 6.65(1H, d, J=2.7Hz), 6.83(1H, d, J=2.7Hz), 6.84–7.01(3H, m), 7.18–7.45(7H, m) | 2940, 2820, 1660, 1630, 1600, 1480, 1375, 1135, 1005, 990 | 63 | |
| 21 | Pale yellow oil | 1.21–1.44(8H, m), 1.52(2H, m), 1.82(2H, m), 2.37(2H, m), 2.49–2.73(6H, m), 3.21(4H, m), 3.62(2H, m), 4.37(2H, t, J=7.3Hz), 4.80(2H, s), 6.64(1H, d, J=3.3Hz), 6.78–7.02(4H, m), 7.18–7.44(7H, m) | 2930, 1660, 1630, 1595, 1485, 1370, 1105 | 78 | |
| 22 | Colorless prism crystals 96.0–98.0° C. (chloroform-isopropyl ether) | 1.55(2H, m), 1.86(2H, m), 2.41(2H, m), 2.57(4H, m), 2.79(2H, m), 3.08–3.30(m), 3.21(s) (7H in total), 3.71(2H, m), 4.36(2H, t, J=7.3Hz), 6.65(1H, d, J=3.3Hz), 6.75–7.00(4H, m), 7.26(2H, m) | 2940, 2820, 1630, 1600, 1405, 1395, 1260, 1025, 910 | 81 | |

TABLE 1-continued

| Comp'd No. | Property Melting point (recrystalli- zation solvent) | NMR*1 (δ ppm 270 MHz) | IR*2 (cm⁻¹) | Yield (%) | Structural formula |
|---|---|---|---|---|---|
| 23 | Colorless oil | 1.32(2H, m), 1.53(2H, m), 1.84(2H, m), 2.38(2H, m), 2.58(4H, t, J=3.4Hz), 2.78(2H, m), 3.10–3.27(m), 3.20(s) (7H in total), 3.70(2H, m), 4.32(2H, t, J=7.3Hz), 6.64(1H, d, J=2.6Hz), 6.79(1H, d, J=2.6Hz), 6.85(1H, t, J=7.6Hz), 6.92(2H, d, J=7.9Hz), 7.26(2H, m) | 2930, 2810, 1625, 1595, 1480, 1390, 905 | 75 | |
| 24 | Colorless prism crystals 135.0–137.0° C. (ethyl acetate- hexane) | 1.51(2H, m), 1.77(2H, m), 2.00–2.17(2H, m), 2.24(1H, m), 2.38(2H, m), 2.50–2.62(4H, m), 3.11(3H, s), 3.17–3.24(4H, m), 3.33(1H, ddd, J=14.6Hz, 7.6Hz, 3.3Hz), 3.50(1H, ddd, J=14.6Hz, 7.6Hz, 3.3Hz), 4.28(2H, m), 4.87(1H, m), 6.15(1H, d, J=2.6Hz), 6.76(1H, d, J=2.6Hz), 6.84(1H, t, J=7.6Hz), 6.92(2H, d, J=7.6Hz), 7.26(2H, m) | (KBr) 3356, 2947, 1602, 1486, 1230, 993, 927 | 89 | |
| 25 | Yellow oil | 1.55(2H, m), 1.87(2H, m), 2.42(2H, m), 2.58(4H, m), 3.12(3H, s), 3.20(4H, m), 3.67(2H, t, J=6.6Hz), 4.38(2H, d, J=7.3Hz), 5.97(1H, dt, J=6.6Hz, 9.6Hz), 6.09(1H, d, J=2.7Hz), 6.75(1H, d, J=9.6Hz), 6.78–6.98(4H, m), 7.26(2H, m) | 2945, 2820, 1600, 1495, 1400, 1310, 1135, 1070, 1000, 910 | 78 | |

TABLE 1-continued

| Comp'd No. | Property Melting point (recrystallization solvent) | NMR*1 (δ ppm 270 MHz) | IR*2 (cm⁻¹) | Yield (%) | Structural formula |
|---|---|---|---|---|---|
| 26 | Colorless needle crystals 164.0–165.0° C. (methanol-isopropyl ether) | 1.32(2H, m), 1.58(2H, m), 1.79(2H, m), 2.40(2H, m), 2.62(4H, t, J=4.6Hz), 2.93(2H, m), 3.11(3H, s), 3.20(4H, t, J=4.6Hz), 3.53(2H, m), 4.25(2H, t, J=7.0Hz), 6.33(1H, d, J=2.7Hz), 6.72(1H, d, J=2.7Hz), 6.85(1H, t, J=7.2Hz), 6.94(2H, d, J=7.9Hz), 7.26(2H, m), 10.15(1H, br.s) | 3565, 2940, 2815, 1620, 1600, 1490, 1400, 1085, 1000, 940, 900, 845 | 95 | |
| 27 | Colorless plate crystals 230.0–236.0° C. (methanol-isopropyl ether) | (DMSO-D₆/TMS) 1.57–1.83(4H, m), 2.81(2H, m), 3.02(3H, s), 3.04–3.21(6H, m), 3.41–3.61(4H, m), 3.79(2H, m), 4.24(2H, m), 6.27(1H, d, J=2.7z), 6.86(1H, t, J=7.3Hz), 6.92–7.10(3H, m), 7.17–7.32(2H, m), 10.71(1H, br.s) | (KBr) 3234, 2936, 2594, 1601, 1497, 1398, 1246, 968, 948, 902, 766 | 90 | |
| 28 | Pale brown prism crystals 115.0–116.0° C. (ethyl acetate-hexane) | 1.55(2H, m), 1.86(2H, m), 2.41(2H, t, J=7.3Hz), 2.57(4H, dd, J=5.3Hz, 4.6Hz), 2.78(2H, m), 3.11(4H, dd, J=5.3Hz, 4.6Hz), 3.20(3H, s), 3.72(2H, m), 4.35(2H, t, J=7.3Hz), 6.64(1H, d, J=3.3Hz), 6.81(1H, d, J=7.3Hz), 6.77–7.02(4H, m) | 2930, 2810, 1655, 1630, 1480, 1390, 905 | 96 | |

TABLE 1-continued

| Comp'd No. | Property Melting point (recrystallization solvent) | NMR*1 (δ ppm 270 MHz) | IR*2 (cm$^{-1}$) | Yield (%) | Structural formula |
|---|---|---|---|---|---|
| 29 | Colorless needle crystals 203.0–205.0° C. (ethanol) | 1.53(2H, m), 1.80(2H, m), 2.41(2H, m), 2.59(4H, t, J=7.3Hz), 2.96(2H, m), 3.02–3.21(m), 3.12(s)(7H in total), 3.55(2H, m), 4.29(2H, t, J=6.9Hz), 6.33(1H, d, J=2.9Hz), 6.75(1H, d, J=2.9Hz), 6.80–7.03(4H, m), 9.51(1H, br.s) | 3575, 2940, 2815, 1625, 1500, 1400, 940, 895 | 91 | *structure: pyrrole-fused azepinone with =NOH, N-CH$_3$ amide, N-(CH$_2$)$_4$-piperazinyl-4-fluorophenyl* |
| 30 | Colorless needle crystals 112.0–113.0° C. (ethyl acetate) | 1.55(2H, m), 1.86(2H, m), 2.40(2H, t, J=7.3Hz), 2.50–2.60(4H, m), 2.78(2H, m), 3.21–3.27(m), 3.21(s) (7H in total), 3.71(2H, m), 4.35(2H, t, J=7.3Hz), 6.64(1H, d, J=3.0Hz), 6.72–6.90(4H, m), 7.15(1H, t, J=8.3Hz) | 2950, 2830, 1660, 1635, 1595, 1485, 1400, 1150, 990, 945 | 86 | *structure: pyrrole-fused azepinone with =O, N-CH$_3$ amide, N-(CH$_2$)$_4$-piperazinyl-3-chlorophenyl* |
| 31 | Colorless prism crystals 179.0–181.0° C. (methanol) | 1.54(2H, m), 1.80(2H, m), 2.40(2H, t, J=7.2Hz), 2.50–2.60(4H, m), 2.93(2H, m), 3.11(3H, s), 3.15–3.25(4H, m), 3.55(2H, m), 4.28(2H, t, J=7.2Hz), 6.33(1H, d, J=3.0Hz), 6.70–6.84(3H, m), 6.86(1H, m), 7.15(1H, t, J=7.9Hz), 9.99(1H, br.s) | 3580, 2950, 2840, 1630, 1600, 1485, 1410, 995, 950 | 61 | *structure: pyrrole-fused azepinone with =NOH, N-CH$_3$ amide, N-(CH$_2$)$_4$-piperazinyl-3-chlorophenyl* |

TABLE 1-continued

| Comp'd No. | Property Melting point (recrystalli- zation solvent) | NMR*1 (δ ppm 270 MHz) | IR*2 (cm$^{-1}$) | Yield (%) | Structural formula |
|---|---|---|---|---|---|
| 32 | Colorless needle crystals 123.0–124.5° C. (ethyl acetate) | 1.54(2H, m), 1.86(2H, m), 2.40(2H, t, J=7.3Hz), 2.50–2.60(4H, m), 2.79(2H, m), 3.10–3.20(4H, m), 3.21(3H, s), 3.73(2H, m), 4.35(2H, t, J=7.3Hz), 6.64(1H, d, J=2.7Hz), 6.80(1H, d, J=2.7Hz), 6.82(2H, dd, J=8.6Hz, 2.0Hz), 7.19(2H, dd, J=8.6Hz, 2.0Hz) | 2950, 2830, 1660, 1620, 1600, 1490, 1395, 1150, 910 | 74 | (structure: pyrrole-fused ketone lactam with N-CH$_3$, linked via (CH$_2$)$_4$ to piperazine-N-(4-chlorophenyl)) |
| 33 | Colorless prism crystals 187.0–189.0° C. (methanol) | 1.53(2H, m), 1.82(2H, m), 2.39(2H, t, J=7.3Hz), 2.50–2.60(4H, m), 2.96(2H, m), 3.10–3.20(m), 3.13(s) (7H in total), 3.55(2H, m), 4.30(2H, t, J=7.3Hz), 6.36(1H, d, J=2.6Hz), 6.77(1H, d, J=2.6Hz) 6.83(2H, dd, J=8.6Hz, 2.0Hz), 7.19(2H, dd, J=8.6Hz, 2.0Hz), 7.83(1H, br.s) | 3580, 2950, 2830, 1630, 1495, 1400 1000, 895 | 90 | (structure: same as 32 but C=O replaced by C=NOH) |
| 34 | Colorless oil | 1.57(2H, m), 1.85(2H, m), 2.45(2H, m), 2.52–2.74(4H, m), 2.79(2H, dd, J=6.6Hz, 4.0Hz), 2.97–3.18(4H, m), 3.21(3H, s), 3.70(2H, m), 3.86(2H, s), 4.36(2H, t, J=7.3Hz), 6.64(1H, d, J=3.0Hz), 6.81(1H, d, J=3.0Hz), 6.83–7.06(5H, m) | (film) 2940, 2816, 1634, 1487, 1392, 1241, 1026 | 92 | (structure: pyrrole-fused ketone lactam with N-CH$_3$, linked via (CH$_2$)$_4$ to piperazine-N-(2-methoxyphenyl)) |

TABLE 1-continued

| Comp'd No. | Property Melting point (recrystallization solvent) | NMR*1 (δ ppm 270 MHz) | IR*2 (cm⁻¹) | Yield (%) | Structural formula |
|---|---|---|---|---|---|
| 35 | Colorless oil | 1.36(2H, m), 1.58(2H, m), 1.84(2H, m), 2.41(2H, t, J=7.2Hz), 2.55–2.75(4H, m), 2.78(2H, t, J=5.2Hz), 3.00–3.20(4H, m), 3.21(3H, s), 3.71(2H, t, J=5.2Hz), 3.86(3H, s), 4.33(2H, t, J=7.2Hz), 6.64(1H, d, J=2.6Hz), 6.80(1H, d, J=2.6Hz), 6.82–7.05(4H, m) | 2900, 2800, 1625, 1470, 1380, 1100, 900 | 99 | *(structure: N-CH₃ azepinone fused pyrrole with (CH₂)₅-piperazine-2-methoxyphenyl)* |
| 36 | Pale yellow oil | 1.38(2H, m), 1.59(2H, m), 1.87(2H, m), 2.41(2H, t, J=7.2Hz), 2.50–2.75(6H, m), 3.00–3.20(4H, m), 3.63(2H, m), 3.86(3H, s), 4.39(2H, t, J=7.2Hz), 4.80(2H, s), 6.65(1H, d, J=2.6Hz), 6.82(1H, d, J=2.6Hz), 6.82–7.05(4H, m), 7.25–7.40(5H, m) | 2950, 2830, 1660, 1630, 1490, 1380, 1110, 910 | 89 | *(structure: N-CH₂Ph azepinone fused pyrrole with (CH₂)₅-piperazine-2-methoxyphenyl)* |
| 37 | Pale yellow needle crystals 114.0–115.5° C. (ethyl acetate-hexane) | 1.57(2H, m), 1.87(2H, m), 2.42(2H, t, J=7.6Hz), 2.50(4H, m), 2.79(2H, m), 3.21(3H, s), 3.71(2H, m), 3.82(4H, m), 4.35(2H, t, J=7.3Hz), 6.49(1H, t, J=4.6Hz), 6.64(1H, d, J=3.0Hz), 6.81(1H, d, J=3.0Hz), 8.30(2H, d, J=4.6Hz). | (KBr) 1661, 1618, 1587, 1553, 1479, 1439, 1357, 1258, 982, 810, 780 | 83 | *(structure: N-CH₃ azepinone fused pyrrole with (CH₂)₄-piperazine-2-pyrimidinyl)* |

TABLE 1-continued

| Comp'd No. | Property Melting point (recrystalli- zation solvent) | NMR*1 (δ ppm 270 MHz) | IR*2 (cm−1) | Yield (%) | Structural formula |
|---|---|---|---|---|---|
| 38 | Colorless prism crystals 196.5–198.0° C. (decomposed) (isopropyl alcohol) | 1.54(2H, m), 1.79(2H, m), 2.39(2H, m), 2.48(4H, t, J=4.9Hz), 2.95(2H, m), 3.12 (3H, s), 3.56(2H, m), 3.83(4H, t, J=4.9Hz), 4.30(2H, t, J=7.3Hz), 6.35(1H, d, J=2.6Hz), 6.47(1H, t, J=4.6Hz), 6.76(1H, d, J=2.6Hz), 8.31(2H, d, J=4.6Hz), 9.23 (1H.br.s) | (KBr) 3262, 1585, 1546, 1486, 1438, 1358, 1244, 984, 945, 902, 800, 778 | 91 | |
| 39 | Pale yellow oil | 1.57(2H, m), 1.86(2H, m), 2.41(2H, t, J=7.3Hz), 2.49–2.61(4H, m), 2.79(2H, dd, J=6.6Hz, 4.0Hz), 3.21(3H, s), 3.45–3.62(4H, m), 3.71(2H, m), 4.36(2H, t, J=7.3Hz), 6.57–6.72(3H, m), 6.81(1H, d, J=2.7Hz), 7.46(1H, dt, J=2.0Hz, 4.3Hz), 8.18(1H, m) | (film) 2942, 1654, 1636, 1593, 1483, 1437, 1390, 1244 | 96 | |
| 40 | Pale yellow oil | 1.26(3H, t, J=7.3Hz), 1.51(2H, m), 1.84(2H, m), 2.23–2.46(6H, m), 2.79(2H, m), 3.20(3H, s), 3.47(4H, t, J=5.3Hz), 3.71(2H, m), 4.13(2H, q, J=7.3Hz), 4.34(2H, t, J=7.3Hz), 6.64(1H, d, J=3.0Hz), 6.79(1H, d, J=3.0Hz) | (film) 3508, 2937, 1694, 1634, 1527, 1487, 1246, 1129, 997 | 74 | |

TABLE 1-continued

| Comp'd No. | Property Melting point (recrystallization solvent) | NMR*1 (δ ppm 270 MHz) | IR*2 (cm⁻¹) | Yield (%) | Structural formula |
|---|---|---|---|---|---|
| 41 | Colorless oil | 1.51(2H, m), 1.81(2H, m) 2.19–2.68(m), 2.37(t, J=7.3Hz) (10H in total), 2.76(2H, m), 3.18(3H, s), 3.51(2H, s), 3.67(2H, m), 4.32(2H, t, J=7.3Hz), 6.62(1H, d, J=2.7Hz), 6.78(1H, d, J=2.7Hz), 7.16–7.48(5H, m) | (film) 2940, 1634, 1527, 1487, 1392, 1243, 1152, 1012 | 85 | (structure: N-CH₃ azepinone fused to pyrrole with N-(CH₂)₄-piperazine-NCH₂-phenyl) |
| 42 | Colorless oil (hydrochloride) Colorless powdery crystals 178.0–183.0° C. (methanol-ethyl acetate-isopropyl ether) | 1.52(2H, m), 1.85(2H, m), 2.23–2.60(m), 2.39(t, J=7.3Hz)(6H in total), 2.78(2H, dd, J=6.6Hz, 4.0Hz), 3.20(3H, s), 3.30–3.90(6H, m), 4.33(2H, t, J=7.3Hz), 6.63(1H, d, J=3.0Hz), 6.79(1H, d, J=3.0Hz), 7.32–7.49(5H, m) | (film) 2937, 1633, 1527, 1487, 1434, 1392, 1244, 1017 | 85 | (structure: N-CH₃ azepinone fused to pyrrole with N-(CH₂)₄-piperazine-N-C(=O)-phenyl) |
| 43 | Colorless oil (hydrochloride) Colorless crystals 204.0–208.0° C. (ethyl ether) | 1.55(2H, m), 1.85(2H, m), 2.05(2H, m), 2.40(2H, m), 2.80(2H, m), 3.20(3H, s), 3.40–3.80(8H, m), 4.33(2H, t, J=7.3Hz), 5.09(2H, s), 6.63(1H, d, J=3.3Hz), 6.79(1H, d, J=3.3Hz), 6.98(2H, d, J=8.6Hz), 7.28–7.48(7H, m) | 2900, 1655, 1620, 1420, 1000 | 20 | (structure: N-CH₃ azepinone fused to pyrrole with N-(CH₂)₄-piperazine-N-C(=O)-(4-phenoxyphenyl via OCH₂)) |

TABLE 1-continued

| Comp'd No. | Property Melting point (recrystalli- zation solvent) | NMR*1 (δ ppm 270 MHz) | IR*2 (cm$^{-1}$) | Yield (%) | Structural formula |
|---|---|---|---|---|---|
| 44 | Colorless oil (hydrochloride) Colorless prism Crystals 206.0–215.0° C. (methanol- ethyl ether) | 1.53(2H, m), 1.86(2H, m), 2.39(2H, t, J=7.3Hz), 2.47(4H, m), 2.79(2H, dd, J=6.6Hz, 4.0Hz), 3.21(3H, s), 3.71(2H, m), 3.79(4H, m), 4.34(2H, t, J=7.3Hz), 6.47(1H, dd, J=3.3Hz, 2.0Hz), 6.64(1H, d, J=3.0Hz), 6.98(1H, d, J=3.3Hz), 7.48(1H, m) | (film) 2930, 1632, 1526, 1486, 1436, 1392, 1268, 1243, 1020 | 77 | |
| 45 | Pale yellow oil | 1.58(2H, m), 1.82(2H, m), 2.30–2.68(9H, m), 2.78(2H, m), 3.19(3H, s), 3.60–3.78(3H, m), 4.22(1H, s), 4.32(2H, t, J=7.2Hz), 6.62(1H, d, J=3.3Hz), 6.78(1H, d, J=3.3Hz), 7.12–7.49(10H, m) | 2900, 2800, 1655 1630, 1470, 1100 | 80 | |
| 46 | Pale yellow oil | 1.53(2H, m), 1.82(2H, m), 2.30–2.69(10H, m), 2.78(2H, m), 3.18(2H, m), 3.20(3H, s), 3.69(2H, m), 4.33(2H, m), 6.20–6.35(1H, m), 6.52(1H, d, J=16.8Hz), 6.63(1H, d, J=3.3Hz), 6.78(1H, d, J=3.3Hz), 7.17–7.42(5H, m) | 2900, 2800, 1650, 1630, 1470, 1100, | 60 | |

TABLE 1-continued

| Comp'd No. | Property Melting point (recrystallization solvent) | NMR*1 (δ ppm 270 MHz) | IR*2 (cm⁻¹) | Yield (%) | Structural formula |
|---|---|---|---|---|---|
| 47 | Colorless oil | 1.50(2H, m), 1.82(2H, m), 2.30-2.83(14H, m), 3.20(3H, s), 3.68(2H, m), 3.99(1H, m), 4.30(4H, m), 6.63(1H, d, J=3.3Hz), 6.80(1H, d, J=3.3Hz), 6.85(4H, m) | 2900, 2800, 1650 1630, 1590, 1475, 1100 | 63 | (structure: N-methyl azepine-pyrrole fused ketone with piperazine-(CH$_2$)$_4$- linker to 1,4-benzodioxan-2-ylmethyl) |
| 48 | Colorless oil (hydrochloride) Colorless crystals (ethyl ether) | 1.53(2H, m), 1.85(2H, m), 2.27-2.60(6H, m), 2.78(2H, m), 3.20(3H, s), 3.35-3.90(6H, m), 4.33(2H, t, J=7.3Hz), 6.64(1H, d, J=3.3Hz), 6.78(2H, d, J=8.6Hz), 6.80(1H, d, J=3.3Hz), 7.25(2H, d, J=8.6Hz) | 3300, 2940, 1660, 1625, 1480, 1430, 1000 | 65 | (structure: N-methyl azepine-pyrrole fused ketone with piperazine-(CH$_2$)$_4$- linker to 4-hydroxybenzoyl) |
| 49 | Pale yellow oil | 1.73-1.92(4H, m), 2.79(2H, m), 3.21(3H, s), 3.69(2H, m), 4.00(2H, t, J=6.3Hz), 4.30(2H, t, J=6.3Hz), 6.64(1H, d, J=3.3Hz), 6.76(1H, d, J=3.3Hz), 6.92(1H, s), 7.07(1H, s), 7.60(1H, s) | 2970, 1655, 1630, 1480, 1390, 1105, 905 | 58 | (structure: N-methyl azepine-pyrrole fused ketone with -(CH$_2$)$_2$-imidazolyl substituent) |

TABLE 1-continued

| Comp'd No. | Property Melting point (recrystalli- zation solvent) | NMR*1 (δ ppm 270 MHz) | IR*2 (cm⁻¹) | Yield (%) | Structural formula |
|---|---|---|---|---|---|
| 50 | Colorless oil (hydrochloride) 205.0–211.0° C. (ethanol- ethyl ether) | 2.27(6H, s), 2.50–2.67(3H, m), 2.69(2H, t, J=6.6Hz), 3.65(2H, m), 4.48(2H, t, J=6.6Hz), 4.80(2H, s), 6.64(1H, d, J=2.6Hz), 6.88(1H, d, J=2.6Hz), 7.24–7.42(5H, m) | (film) 2944, 1660, 1633, 1526, 1486, 1373, 1244, 1210 | 77 | (structure with N-CH₂-phenyl, (CH₂)₂NMe₂) |
| 51 | Colorless oil | 1.11(9H, s), 2.50–2.67(3H, m), 2.77(1H, dd, J=4.0Hz, 11.6Hz), 3.35(1H, br.), 3.67(2H, m), 3.96(1H, m), 4.36(1H, dd, J=7.9Hz, 13.9Hz), 4.52(1H, dd, J=4.0Hz, 13.9Hz), 4.77(1H, d, J=14.5Hz), 4.81(1H, d, J=14.5Hz), 6.67(1H, d, J=3.0Hz), 6.97(1H, d, J=3.0Hz), 7.25–7.40(5H, m) | (film) 2965, 1660, 1632, 1529, 1485, 1437, 1374, 1244, 752 | 57 | (structure with CH₂CHCH₂NHC(CH₃)₃, OH) |
| 52 | Brown oil | 2.44(1H, dd, J=12.5Hz, 8.6Hz), 2.54(1H, dd, J=12.5Hz, 4.6Hz), 2.65(4H, m), 2.75(2H, m), 3.20(4H, t, J=4.9Hz), 3.66(2H, m), 4.13(1H, m), 4.34(1H, dd, J=13.9Hz, 6.6Hz), 4.62(1H, dd, J=13.9Hz, 2.6Hz), 4.76(1H, d, J=15.2Hz), 4.82(1H, d, J=15.2Hz), 6.67(1H, d, J=2.6Hz), 6.80–6.96(3H, m), 6.99(1H, d, J=2.6Hz), 7.18–7.41(7H, m) | (film) 3420, 2823, 1629, 1527, 1485, 1243, 1142, 1009, 925 | 76 | (structure with CH₂CHCH₂-N(phenylpiperazine), OH) |

TABLE 1-continued

| Comp'd No. | Property Melting point (recrystallization solvent) | NMR*1 (δ ppm 270 MHz) | IR*2 (cm$^{-1}$) | Yield (%) | Structural formula |
|---|---|---|---|---|---|
| 53 | Pale yellow oil | 1.56(2H, m), 1.75(1H, br.s), 1.90(2H, m), 2.60(2H, m), 2.71(2H, t, J=7.3Hz), 2.98(2H, t, J=5.3Hz), 3.61(2H, m), 4.10(2H, t, J=5.3Hz), 4.40(2H, t, J=7.3Hz), 4.79(2H, s), 6.64(1H, d, J=3.0Hz), 6.81(1H, d, J=3.0Hz), 6.88(2H, d, J=7.3Hz), 6.95(1H, d, J=7.3Hz), 7.17–7.41(7H, m) | 2920, 1655, 1620, 1595, 1480, 1260, 1020 | 55 | |
| 54 | Pale yellow oil (hydrochloride) Pale yellow needle crystals 150.0–155.0° C. (ethanol-isopropyl ether) | 1.55(2H, m), 1.87(2H, m), 2.46(1H, br.s), 2.62–2.86(4H, m), 3.00(2H, t, J=5.3Hz), 3.18(3H, s), 3.70(2H, m), 4.07(2H, t, J=5.3Hz), 4.33(2H, t, J=7.3Hz), 6.62(1H, d, J=3.0Hz), 6.79(1H, d, J=3.0Hz), 6.91(2H, dd, J=1.3Hz, 8.2Hz), 6.95(1H, dd, J=1.3Hz, 8.2Hz), 7.28(2H, t, J=8.2Hz) | 2940, 1660, 1635, 1600, 1490, 1395, 1105, 915 | 64 | |
| 55 | Colorless needle crystals 101.5–103.5° C. (ethanol-isopropyl ether) | 1.53(2H, m), 1.82(2H, m), 2.10(1H, br.s), 2.70(2H, t, J=7.3Hz), 2.91(1H, m), 2.99 (2H, t, J=5.3Hz), 3.09(3H, s), 3.52(2H, m), 4.08(2H, t, J=5.3Hz), 4.28(2H, t, J=7.3Hz), 6.31(1H, d, J=2.9Hz), 6.73(1H, d, J=2.9Hz), 6.85–7.00(3H, m), 7.27(2H, t, J=7.9Hz) | (KBr) 3292, 1623, 1597, 1485, 1404, 1298, 1242, 1055, 974, 908, 778, 756 | 41 | |

TABLE 1-continued

| Comp'd No. | Property Melting point (recrystalli- zation solvent) | NMR*1 (δ ppm 270 MHz) | IR*2 (cm⁻¹) | Yield (%) | Structural formula |
|---|---|---|---|---|---|
| 56 | Colorless oil | 1.62(2H, m), 1.73–1.96(4H, m) 2.64(2H, m), 2.77(2H, m), 3.08–3.28(m), 3.19(s)(5H in total), 3.68(2H, m), 4.06(2H, t, J=6.3Hz), 4.34(2H, t, J=7.3Hz), 4.83(1H, br.s), 6.63(1H, d, J=2.7Hz), 6.79(1H, d, J=2.7Hz), 7.09–7.22(3H, s), 7.22–7.35(2H, m) | 3440, 2950, 1710, 1630, 1480, 905 | 41 | (structure) |
| 57 | Pale yellow oil | 0.92(3H, t, J=7.3Hz), 1.28(2H, m), 1.55–2.00(6H, m), 2.20(1H, m), 2.52–2.95(8H, m), 2.96–3.10(1H, m), 3.20(3H, m), 3.68(3H, m), 4.33(2H, t, J=7.0Hz),6.63(1H, m,), 4.67(1H, d, J=3.3Hz), 6.70(1H, d, J=11.0Hz), 6.83(1H, d, J=3.3Hz), 6.98(1H, t, J=11.0Hz) | 3250, 2920, 1655, 1630, 1580, 1460, 1100, 900 | 37 | (structure) |

*1: Measured in CDCl₃ with TMS as an internal standard unless otherwise specifically indicated.
*2: Measured as a CHCl₃ solution unless otherwise specifically indicated.

Test

With respect to certain compounds of the present invention, their anti-$\alpha_1$ action and anti-serotonin (5-HT) action were investigated by the testing methods which will be described below. The test results of some representative compounds are tabulated below.

(1) Anti-$\alpha_1$ action

The thoracic aorta of each Hartley male guinea pig (body weight: 300–500 g) was excised. A sample cut in a helical form was suspended under 1 g load in a Magnus cylinder filled with the Tyrode solution of 37° C. which had been saturated with a mixed gas consisting of 95% $O_2$+5% $CO_2$. Using an isometric transducer ("TB-612J"/NIHON KOHDEN) and a pressure preamplifier ("AP-620G"/NIHON KOHDEN), variations in tension were measured. The measurement results were recorded on a thermal pen-writing recorder ("WT-647G"/NIHON KOHDEN).

Taking the tonic contraction induced by $10^{-5}$ M norepinephrine (NE) as 100% the percent contractions upon addition of each test drug at $10^{-8}$ and $10^{-7}$ M were determined as anti-$\alpha_1$ action.

(2) Anti-serotonin action (anti-5-HT action)

The superior mesenteric artery of each Hartley male guinea pig (body weight: 300–500 g) was excised. A sample cut in a helical form was suspended under 0.3 g load in a Magnus cylinder filled with the Tyrode solution of 37° C. which had been saturated with a mixed gas consisting of 95% $O_2$+5% $CO_2$. Using an isometric transducer ("UL-10"/SHINKOH K.K.) and a pressure preamplifier ("DSA-605A"/SHINKOH K.K.), variations in tension were measured. The measurement results were recorded on a pen-writing recorder ("VP-6537A"/NATIONAL K.K.). Taking the contraction induced by $10^{-5}$ M serotonin (5-HT) as 100% the percent contractions in the presence of each test drug at $10^{-7}$ and $10^{-6}$ M were determined as anti-5-HT action.

| | (Results) | | | |
|---|---|---|---|---|
| | Anti $\alpha_1$, action (% of Control) | | Anti 5-HT action (% of Control) | |
| Comp'd No. | $10^{-8}$M | $10^{-7}$M | $10^{-7}$M | $10^{-6}$M |
| 20* | 49.2 | 19.9 | 54.5 | 45.7 |
| 24 | 90.3 | 41.0 | 78.3 | 36.0 |
| 27 | 74.2 | 18.4 | 69.8 | 25.7 |
| 29 | 94.2 | 39.5 | 66.2 | 12.0 |
| 31 | 93.9 | 19.4 | 86.2 | 69.0 |
| 36* | 43.6 | 21.4 | 84.0 | 61.8 |

*The test compound was obtained by converting the compound to its hydrochloride with excess hydrogen chloride in an organic solvent and, if necessary, subjecting the hydrochloride to recrystallization.

Industrial Applicability

The pyrroloazepine derivatives according to the present invention are drugs having excellent anti-$\alpha_1$ action and anti-serotonin action and feature high safety. They can therefore be used, for example, as novel therapeutics for circulatory diseases.

It is claimed:

1. A pyrroloazepine represented by the following formula (I):

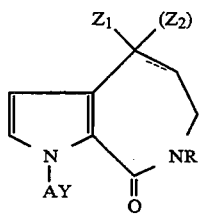

wherein the dashed line indicates the presence or absence of a bond and when the bond indicated by the dashed line is present, $Z_1$ represents a hydrogen atom but, when the bond indicated by the dashed line is absent, $Z_1$ represents a hydrogen atom and $Z_2$ represents a hydroxyl group or $Z_1$ and $Z_2$ are taken together to form an oxygen atom or a group $NOR_1$ in which $R_1$ represents a hydrogen atom, a branched or linear $C_{1-4}$ alkyl group, a $C_{6}$-$C_{10}$ aryl group or $C_{8}$-$C_{16}$ aralkyl group, said aryl or aralkyl group optionally substituted by one or more halogen atoms, $C_1$-$C_4$ alkyl groups, or $C_1$-$C_4$ alkoxy groups; R represents a hydrogen atom, a branched or linear $C_{1-8}$ alkyl group, a $C_{3-8}$ cycloalkyl group, a $C_{3-8}$ cycloalkyl-alkyl group, a $C_{6-10}$ aryl or $C_{7-20}$ aralkyl group, said aryl or aralkyl group optionally substituted by one or more halogen atoms, $C_{1-4}$ alkyl groups, and/or $C_{1-4}$ alkoxy groups; A represents a branched or linear $C_{2-10}$ alkylene, a branched or linear $C_{4}$-$C_{10}$ alkenylene, or a branched or linear $C_{4-10}$ alkynylene group, said alkylene, alkenylene, or alkynylene optionally having one or more hydrogen atoms substituted by a hydroxyl group; and Y represents a group:

in which $R_2$ and $R_3$ may be the same or different and individually represent a hydrogen atom, a branched or linear $C_{1-8}$ alkyl group which may be substituted by a lower alkoxy group or a $C_{6-10}$ aryloxyl group, a $C_{6-10}$ aryl group, a $C_{7-20}$ aralkyl group or a partially-saturated naphthyl group, said aryloxyl, aryl, aralkyl, or partially-saturated naphthyl group optionally substituted-by one or more halogen atoms, $C_{1-4}$ alkyl groups, $C_{1-4}$ alkoxy groups, and/or hydroxyl groups, or a group:

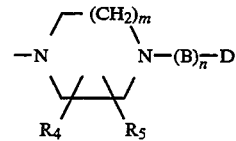

in which $R_4$ and $R_5$ may be the same or different and individually represent a hydrogen atom or a branched or linear $C_{1-8}$ alkyl group; B represents a carbonyl group, a sulfonyl group, a $C_{1-10}$ alkylene group, a $C_{2-10}$ alkenylene, or a phenylmethylene group optionally substituted by one or more halogen atoms, $C_{1-4}$ alkyl groups, or $C_{1-4}$ alkoxy groups; m stands for 1 or 2; n stands for 0 or 1; and D represents a $C_{1-4}$ alkoxy group, a pyridyl, pyrimidyl or furanyl group, a $C_{6-10}$ aryl group optionally substituted with one or more hydroxyl groups, halogen atoms, $C_{1-4}$ alkyl groups, $C_{1-4}$ alkoxy groups, and/or benzyloxy groups or a 1,4-benzodioxanyl group, or a physiologically acceptable salt thereof.

2. A pyrroloazepine or a salt thereof according to claim 1, wherein in the formula (I), $Z_1$ and $Z_2$ are taken together to form an oxygen atom or a group $NOR_1$, $R_1$ having the same meaning as defined above.

3. A pyrroloazepine or a salt thereof according to claim 1, wherein in the formula (I), Y represents a group:

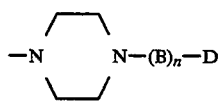

wherein B, D and n have the same meanings as defined above.

4. A process for the preparation of a pyrroloazepine represented by the following formula (Ia):

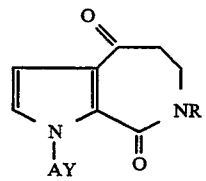

(Ia)

wherein A, R and Y have the same meanings as defined above, which comprises:
  causing a compound, which is represented by the following formula (III):

 (III)

wherein A has the same meaning as defined above and X and X' may be the same or different and individually mean a substituent easily replaceable with an amino group, to act on a compound represented by the following formula (II):

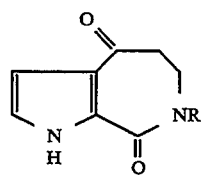

(II)

wherein R has the same meaning as defined above to obtain a compound represented by the following formula (IV):

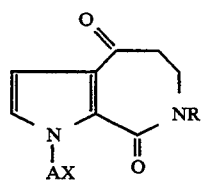

(IV)

wherein A, R and X have the same meanings as defined above; and then
  reacting the compound of the formula (IV) with a nitrogen-containing compound represented by the following formula (V):

 (V)

wherein Y has the same meaning as defined above.

5. A process for the preparation of a pyrroloazepine represented by the following formula (Ib):

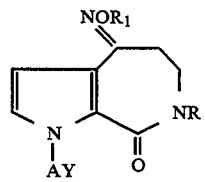

(Ib)

wherein A, R, $R_1$ and Y have the same meanings as defined above, which comprises:
  causing a hydroxylamine or a derivative thereof, which is represented by the following formula (VI):

 (VI)

wherein $R_1$ has the same meaning as defined above, to act on a compound represented by the following formula (Ia):

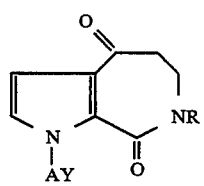

(Ia)

wherein A, Y and R have the same meanings as defined above.

6. A process for the preparation of a pyrroloazepine represented by the following formula (Ib):

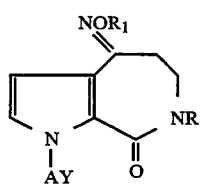

(Ib)

wherein A, Y, R and $R_1$ have the same meanings as defined above, which comprises:
  causing a hydroxylamine or a derivative thereof, which is represented by the following formula (VI):

 (VI)

wherein $R_1$ has the same meanings as defined above, to act on a compound represented by the following formula (IV):

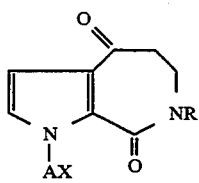

(IV)

wherein A, X and R have the same meanings as defined above, thereby forming a compound represented by the following formula (VII):

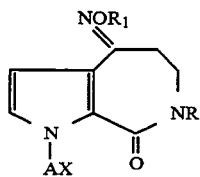

wherein A, R, $R_1$ and X have the same meanings as defined above; and reacting the compound of the formula (VII) with a nitrogen-containing compound represented by the following formula (V):

H—Y  (V)

wherein Y has the same meaning as defined above.

7. A process for the preparation of a pyrroloazepine represented by the following formula (Ic):

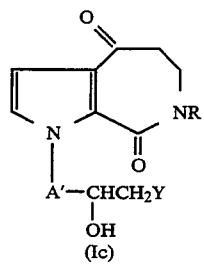

wherein A' represents an alkylene group, and R and Y have the same meanings as defined above, which comprises:

causing a compound represented by the formula (VIII):

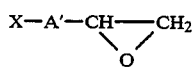

wherein A' and X has the same meanings as defined above to act on a compound represented by the following formula (II):

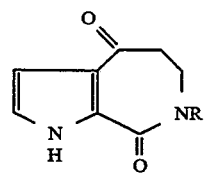

wherein R has the same meaning as defined above, thereby forming a compound represented by the following formula (IX):

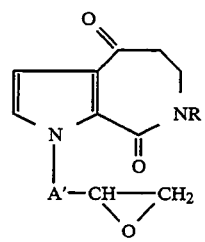

wherein A' and R have the same meanings as defined above; and reacting the compound of the formula (IX) with a nitrogen-containing compound represented by the following formula (V):

H—Y  (V)

wherein Y has the same meaning as defined above.

8. A process for the preparation of a pyrroloazepine represented by the following formula (Ia):

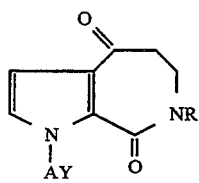

wherein A, R and Y have the same meanings as defined above, which comprises reacting a compound represented by the formula (II):

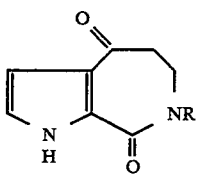

wherein R has the same meaning as defined above with a compound represented by the formula (X):

X—AY  (X)

wherein A, X and Y have the same meanings as defined above.

9. A process for the preparation of a pyrroloazepine represented by the following formula (Id):

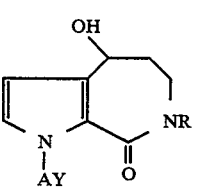

wherein A, R and Y have the same meanings as defined above, which comprises reducing a pyrroloazepine derivative represented by the formula (Ia):

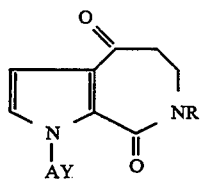

(Ia)

wherein A, R and Y have the same meanings as defined above.

10. A process for the preparation of a pyrroloazepine represented by the following formula (Ie):

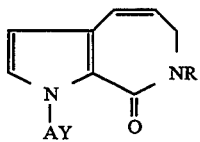

(Ie)

wherein A, R and Y have the same meanings as defined above, which comprises subjecting to dehydration a pyrroloazepine derivative represented by the following formula (Id):

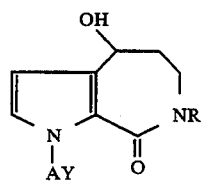

(Id)

wherein A, R and Y have the same meanings as defined above.

11. A compound suitable for use in the production of a pharmaceutical product, said compound being represented by the following formula (IX):

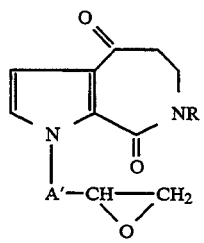

(IX)

wherein A' and R have the same meanings as defined above.

12. A therapeutic agent for circulatory diseases, comprising:
(a) an effective amount of a pyrroloazepine derivative compound of the formula (I) or a salt thereof, as described in claim 1 and (b) a pharmaceutically acceptable carrier.

* * * * *

UNITED STATES PATENT AND TRADEMARK OFFICE
CERTIFICATE OF CORRECTION

PATENT NO. : 5,397,780
DATED : March 14, 1995
INVENTOR(S) : Akira MIZUNO, et al.

It is certified that error appears in the above-indentified patent and that said Letters Patent is hereby corrected as shown below:

On the title page, the Foreign Application Priority Data, Item [30], was omitted. It should read:

--Aug. 7, 1991 [JP] Japan ..............3-221191--

Also on the title page, Item [87], the PCT Publishing Number and Publishing Date are listed incorrectly. They should read:

--[87] PCT Pub. No.:     WO93/03031
       PCT Pub. Date:    Feb. 18, 1993--

Signed and Sealed this

Twelfth Day of December, 1995

BRUCE LEHMAN

*Commissioner of Patents and Trademarks*